United States Patent
Rundlett

(10) Patent No.: US 9,861,452 B2
(45) Date of Patent: Jan. 9, 2018

(54) LOW-VISCOSITY LIQUID RADIATION CURABLE DENTAL ALIGNER MOLD RESIN COMPOSITIONS FOR ADDITIVE MANUFACTURING

(71) Applicant: DSM IP ASSETS BV, TE Heerlen (NL)

(72) Inventor: Beth Rundlett, West Des Moines, IA (US)

(73) Assignee: DSM IP ASSETS B.V., Heerlen (NL)

( * ) Notice: Subject to any disclaimer, the term of this patent is extended or adjusted under 35 U.S.C. 154(b) by 229 days.

(21) Appl. No.: 14/454,091

(22) Filed: Aug. 7, 2014

(65) Prior Publication Data

US 2015/0044623 A1 Feb. 12, 2015

Related U.S. Application Data

(60) Provisional application No. 61/864,302, filed on Aug. 9, 2013.

(51) Int. Cl.
| | | |
|---|---|---|
| A61C 9/00 | (2006.01) | |
| A61C 7/08 | (2006.01) | |
| C08L 63/00 | (2006.01) | |
| C08G 59/22 | (2006.01) | |
| C08G 59/24 | (2006.01) | |

(52) U.S. Cl.
CPC .............. *A61C 7/08* (2013.01); *C08G 59/226* (2013.01); *C08G 59/24* (2013.01); *C08G 59/245* (2013.01); *C08L 63/00* (2013.01)

(58) Field of Classification Search
CPC ........ A61C 7/08; C08G 59/226; C08G 59/24; C08G 59/245; C08L 63/00
USPC ......... 433/6, 24, 229, 48; 525/170, 168, 6, 8
See application file for complete search history.

(56) References Cited

U.S. PATENT DOCUMENTS

| | | |
|---|---|---|
| 5,167,882 A | 12/1992 | Jacobine et al. |
| 5,242,304 A | 9/1993 | Traux et al. |
| 5,434,196 A | 7/1995 | Ohkawa et al. |
| 5,476,748 A | 12/1995 | Steinmann et al. |
| 5,525,645 A | 6/1996 | Ohkawa et al. |
| 5,626,919 A | 5/1997 | Chapman et al. |
| 5,674,922 A | 10/1997 | Igarashi et al. |
| 5,981,616 A | 11/1999 | Yamamura et al. |
| 6,100,007 A | 8/2000 | Pang et al. |
| 6,127,085 A | 10/2000 | Yamamura et al. |
| 6,136,497 A | 10/2000 | Melisaris et al. |
| 6,368,769 B1 | 4/2002 | Ohkawa et al. |
| 6,379,866 B2 | 4/2002 | Lawton et al. |
| 6,413,696 B1 | 7/2002 | Pang et al. |
| 6,558,871 B1 | 5/2003 | Takahashi et al. |
| 6,939,489 B2 | 9/2005 | Moszner et al. |
| 7,183,040 B2 | 2/2007 | Thies et al. |
| 7,232,850 B2 | 6/2007 | Fong et al. |
| 7,261,533 B2 * | 8/2007 | Wrosz ................. A61C 7/00 425/110 |
| 7,365,106 B2 | 4/2008 | Suzuki et al. |
| 7,378,455 B2 | 5/2008 | Lu et al. |
| 8,019,465 B2 | 9/2011 | Spiridonov et al. |
| 8,026,295 B2 | 9/2011 | Walz et al. |
| 8,334,025 B2 | 12/2012 | Fong et al. |
| 8,362,148 B2 | 1/2013 | Messe et al. |
| 8,501,033 B2 | 8/2013 | Southwell et al. |
| 2003/0222366 A1 | 12/2003 | Stangel et al. |
| 2004/0137368 A1 | 7/2004 | Steinmann |
| 2004/0142274 A1 | 7/2004 | Thies et al. |
| 2006/0222999 A1 | 10/2006 | Miyazaki et al. |
| 2007/0004819 A1 | 1/2007 | Lu et al. |
| 2007/0042191 A1 | 2/2007 | Carter et al. |
| 2008/0103226 A1 * | 5/2008 | Xu ..................... C08G 59/22 522/130 |
| 2009/0004579 A1 | 1/2009 | Sarmah et al. |
| 2009/0071602 A1 | 3/2009 | Weippert et al. |
| 2010/0152314 A1 * | 6/2010 | Ito ..................... C08F 283/10 522/170 |

(Continued)

FOREIGN PATENT DOCUMENTS

| | | |
|---|---|---|
| EP | 0848294 | 9/2001 |
| JP | 2000-94453 | 4/2000 |
| JP | 2002-256062 | 9/2002 |

(Continued)

OTHER PUBLICATIONS

Effect of Composition on Performance Properties in Cationic Uvcurable Coating Systems. JCT Research 1.3 (Jul. 2004): 153(9). Nash et al.
Ultraviolet Curing Kinetics of Cycloaliphatic Epdxide With Real-Time Fourier Transform Infrared Spectroscopy. Journal of Applied Polymer Science 90: 2485-2499, 2003. Chen et al.
Specification sheet for 3-methyl-3-oxetanemethanol, Sigma-Aldrich online, available at www.sigmaaldrich.com, and current as of Jul. 19, 2017.

(Continued)

*Primary Examiner* — Michael Carey
(74) *Attorney, Agent, or Firm* — Daniel S. Bujas

(57) ABSTRACT

Liquid radiation curable resin compositions for additive manufacturing comprising: from about 5 to about 30 wt % of an oxetane; a (meth)acrylate component; a cationic photoinitiator; a free-radical photoinitiator; and from about 50 to about 80 wt % of an epoxy, which further comprises a cycloaliphatic epoxy component, and an epoxy component having an aromatic glycidyl ether group, wherein the majority of the epoxy is the cycloaliphatic epoxy component are described and claimed. Also described and claimed is a process for using the liquid radiation curable resins for additive manufacturing to create molds for dental aligners, and the three-dimensional molds made from the liquid radiation curable resins for additive manufacturing.

20 Claims, No Drawings

(56) References Cited

U.S. PATENT DOCUMENTS

2011/0319515 A1   12/2011   Carter et al.

FOREIGN PATENT DOCUMENTS

| WO | 2004-035643 | 4/2004 |
| WO | 2005041804 | 5/2005 |
| WO | 2009-005576 | 1/2009 |

OTHER PUBLICATIONS

OXT Technical Report for Aron Oxetane OXT-101, Toagosei Co., Ltd., available at www.sanyocorp.com/oxetane, current as of Jul. 19, 2017.

\* cited by examiner

LOW-VISCOSITY LIQUID RADIATION CURABLE DENTAL ALIGNER MOLD RESIN COMPOSITIONS FOR ADDITIVE MANUFACTURING

FIELD OF THE INVENTION

The present invention relates to liquid radiation curable resin compositions for additive manufacturing processes.

BACKGROUND OF THE INVENTION

Additive manufacturing processes for producing three dimensional objects are well known. Additive manufacturing processes utilize computer-aided design (CAD) data of an object to build three-dimensional parts. These three-dimensional parts may be formed from liquid resins, powders, or other materials.

A non-limiting example of an additive manufacturing process is stereolithography (SL). Stereolithography is a well-known process for rapidly producing models, prototypes, patterns, and production parts in certain applications. SL uses CAD data of an object wherein the data is transformed into thin cross-sections of a three-dimensional object. The data is loaded into a computer which controls a laser that traces a pattern of a cross section through a liquid radiation curable resin composition contained in a vat, solidifying a thin layer of the resin corresponding to the cross section. The solidified layer is recoated with resin and the laser traces another cross section to harden another layer of resin on top of the previous layer. The process is repeated layer by layer until the three-dimensional object is completed. When initially formed, the three-dimensional object is, in general, not fully cured, and is called a "green model." Although not required, the green model may be subjected to post-curing to enhance the mechanical properties of the finished part. An example of an SL process is described in U.S. Pat. No. 4,575,330.

There are several types of lasers used in stereo lithography, traditionally ranging from 193 nm to 355 nm in wavelength, although other wavelength variants exist. The use of gas lasers to cure liquid radiation curable resin compositions is well known. The delivery of laser energy in a stereolithography system can be Continuous Wave (CW) or Q-switched pulses. CW lasers provide continuous laser energy and can be used in a high speed scanning process. However, their output power is limited which reduces the amount of curing that occurs during object creation. As a result the finished object will need additional post process curing. In addition, excess heat could be generated at the point of irradiation which may be detrimental to the resin. Further, the use of a laser requires scanning point by point on the resin which can be time-consuming.

Other methods of additive manufacturing utilize lamps or light emitting diodes (LEDs). LEDs are semiconductor devices which utilize the phenomenon of electroluminescence to generate light. At present, LED UV light sources currently emit light at wavelengths between 300 and 475 nm, with 365 nm, 390 nm, and 395 nm being common peak spectral outputs. See textbook, "Light-Emitting Diodes" by E. Fred Schubert, $2^{nd}$ Edition, © E. Fred Schubert 2006, published by Cambridge University Press.

Many additive manufacturing applications require a freshly-cured part, aka the "green model" to possess high mechanical strength (modulus of elasticity, fracture strength). This property, often referred to as "green strength," constitutes an important property of the green model and is determined essentially by the nature of the liquid radiation curable resin composition employed in combination with the type of stereolithography apparatus used and degree of exposure provided during part fabrication. Other important properties of a stereolithographic resin composition include a high sensitivity for the radiation employed in the course of curing and a minimum amount of curl or shrinkage deformation, permitting high shape definition of the green model. Of course, not only the green model but also the final cured article should have sufficiently optimized mechanical properties.

Additive manufacturing processes such as stereolithography have long been employed for dental applications. In one common application, a liquid radiation curable resin composition is selectively cured via additive manufacturing processes to produce a plurality of three-dimensional molds, each successive mold representing an incrementally improved realignment position of a patient's teeth. The molds are next post-cured, thermally treated, and cooled. Finally, a thermoplastic sheet is vacuum-formed over the molds to create aligners, which are inserted into a patient's mouth for use in orthodontistry. "Aligners," or "dental aligners," as described herein, are also known in the art as "plastic orthodontic appliances," and are described in, for example, U.S. Pat. No. 8,019,465, assigned to Align Technology, Inc., which is hereby incorporated by reference. The vacuum-forming of dental aligners, which involves the application of considerable force and heat, is described in, for example, U.S. Pat. No. 5,242,304, assigned to Tru-Train, Inc., and is hereby incorporated by reference. From the foregoing, it is imperative that in order to create parts able to withstand the stresses of the dental aligner manufacturing process, the liquid radiation curable resin compositions used to create the molds possess excellent mechanical properties. These mechanical properties can be predicted by measuring the glass transition temperature (Tg) and Young's Modulus.

The finished series of aligners possess visually-imperceptible, but critically different, dimensions to ensure a gradual realignment. Further, the molds must accurately represent the dimensions of a patient's teeth in order to minimize the discomfort associated with wearing an aligner. Therefore, dimensional precision of the initial mold formed via the additive manufacturing process is of paramount importance.

Furthermore, in order to maximize throughput, industry users require that three-dimensional parts must be created via additive manufacturing processes as quickly as possible. This is particularly a requirement in dental applications wherein a multitude of different three-dimensional molds needs to be created for even a single patient to efficiently create a complete set of dental aligners.

Typically, the building process in vat-based additive manufacturing systems is a recurring process consisting of the following repeating steps: 1) the surface of the liquid radiation curable resin composition is exposed to appropriate imaging radiation corresponding to a desired cross-section of the three-dimensional object, thus forming a solid layer; 2) the vertically movable elevator is translated down, further below the surface of the liquid radiation curable resin composition; 3) a mechanical recoater device is translated across the surface of the liquid radiation curable resin composition to assist in forming the next layer of liquid radiation curable resin over the just formed solid layer; and 4) the elevator is translated up such that the distance between the surface of the liquid radiation curable resin and the just formed solid layer of the three-dimensional object is equal to the desired thickness of the layer to be formed.

The speed of the above mentioned process in a vat-based additive manufacturing system is highly affected by the viscosity of the liquid radiation curable resin. Many existing liquid radiation curable resins are highly viscous; that is, they are sufficiently flow-resistant such that they will not readily form a smooth layer of liquid photocurable resin over the just formed solid layer to ensure accurate cure by actinic radiation. With highly viscous resins, forming a new layer of liquid photocurable resin over the top of a previously-cured layer becomes a time consuming process.

First, the viscosity of the resin affects the ability of the liquid radiation curable resin to cover the parts of the just formed solid layer with a fresh, even layer. Consequently, a recoating operation has traditionally been used to simultaneously place and mechanically smooth a fresh layer of resin over a previously cured layer prior to exposure with actinic radiation. In one non-limiting example, this recoating operation has traditionally been performed by means of a "recoating blade." A recoating blade design is discussed in, for example, Chapman et al., U.S. Pat. No. 5,626,919, assigned to DSM IP Assets, B.V.

Second, the viscosity of the liquid radiation curable resin affects the time it takes for the liquid radiation curable resin to reach equilibrium as a smooth, even surface after the recoating step. Consequently, a programmed "dwell time" has been traditionally used between the end of the recoating operation and the beginning of the exposure of the next layer of resin to appropriate imaging radiation. Both the recoating operation and the dwell time dramatically increase the process time of a typical vat-based additive manufacturing process.

Few resins suited for such vat-based additive manufacturing processes possess a sufficiently-low viscosity to provide uniform coverage and a "self-smoothing" nature. Such resins would obviate the need for a time-consuming recoating operation and dwell time, instead allowing a fresh layer to be placed upon a previously-cured layer by means of a process called "deep dipping." Deep dipping is an process whereby a fresh layer of liquid radiation curable resin is applied by merely lowering the elevator deeper into a vat of the liquid radiation curable resin at a specified depth. A resin of sufficiently-low viscosity would therefore allow for the liquid to freely and uniformly flow over the previously cured layer without requirement of assistance from a recoating blade or equilibrating dwell-time.

Third, the viscosity of the liquid radiation curable resin also affects the time and difficulty associated with preparing a recently-cured part for post processing operations. In a vat-based additive manufacturing process, upon build completion of a three-dimensional solid part, the solidified portions are removed from the liquid uncured resin. A highly viscous resin will be more difficult to separate from the cured part, wherein a resin of substantially low viscosity will be removed without significant effort. Thus, low viscosity resins reduce the time required to clean a part in order to prepare it for post processing operations.

While there exist few resins possessing sufficiently low viscosity for suitability to many vast-based additive manufacturing applications, fewer still possess the requisite stability to maintain a low viscosity over time. Liquid radiation curable resins for additive manufacturing possess a well-known tendency to increase in viscosity over time upon exposure to ambient conditions, particularly when stored at elevated temperatures. This exacerbates problems associated with high initial viscosities, resulting in increasingly less efficient, more costly, additive manufacturing processes over time. Viscosity stability of the uncured resin is thus also an important property in a liquid radiation curable resin for additive manufacturing.

In a select few of the more demanding applications of additive manufacturing, users require not only long-term physical property stability in the uncured resin itself, but also of the parts created from the liquid radiation curable resin. Fewer still of the most demanding additionally require that liquid radiation cured parts retain maintenance of superior physical properties over months and even years. One such application, in the dental aligner mold manufacturing industry, further requires liquid radiation cured molds created via additive manufacturing to retain both dimensional and physical stability after severe short- and long-term stresses.

Molds for dental aligners created via additive manufacturing with liquid radiation curable resins undergo multiple, intense, short-term post-processing operations prior to their use in contributing to the formation of a dental aligner. In one process, immediately after cure, the parts are removed from a liquid vat of photocurable resin, cleaned, and then placed in a UV post-cure apparatus, often for several hours. A discussion of UV post-curing of parts created via additive manufacturing techniques can be found in, for example, U.S. Pat. No. 5,167,882, assigned to Loctite Corporation, which is hereby incorporated by reference. Additionally, during the fabrication of dental aligner molds, the post-cured part is then heat treated at various times and temperatures. In one example, parts undergo thermal treatment at 100° Celsius for 6 hours; in another example, parts undergo thermal treatment at 140° Celsius for 6 hours. The mold next undergoes a cooling process. Finally, a dental aligner is vacuum formed against the liquid radiation cured, post-cured, heat treated, and cured mold, which is now also subjected to the additional stresses and heat of the vacuum forming process.

Additionally, manufacturers of dental aligners require that molds produced from liquid radiation curable resins be stored long after their initial use in forming an aligner. This is due to the fact that, over the course of treatment, a patient may lose, misplace, or damage one of their original aligners, thereby necessitating a replacement. Retention of the original molds obviates the time-consuming and costly requirement in producing a new mold via a duplicative set of additive manufacturing, post-curing, and heat-treating processes. However, long-term retention is only viable if the original mold maintains dimensional stability, as a replacement aligner will be faithful only to the mold upon which it is vacuum formed.

The environmental stresses placed on original molds created from liquid radiation curable resins are significant over time. Replacement aligners may not be needed for many months or years. Additionally, in an effort to minimize incurring the energy costs associated with climate-controlled warehouses, inventoried parts are often stored in high heat, light, and humidity environments. Exposure to these conditions over long periods of time has a tendency to induce dimensional change in the molds. Selecting a liquid radiation curable resin that ensures dimensional stability of the molds after intense post-processing, and after long-term ambient exposure, is therefore is of unique paramount importance for the dental aligner industry.

In addition to short and long term dimensional stability, the dental aligner industry requires that molds created from liquid radiation curable resins for additive manufacturing possess superior long-term mechanical strength. First, this ensures that the inventoried molds can withstand physical damage during routine handling and storage. Also it is important that the "aged" molds can withstand the heat and forces exerted by the vacuum forming process associated with forming replacement aligners. A known proxy for measuring long-term mechanical strength after exposure to humidity is known as hydrolytic stability. See, e.g., U.S. Pat. No. 7,183,040, assigned to DSM IP Assets, B.V., for a discussion of hydrolytically stable stereolithography resins. Additionally, achieving consistent Young's Modulus values after long term periodic measurement also tends to evidence superior long-term physical durability of a liquid radiation cured part.

In order to achieve the desired balance of properties, different types of resin systems have been proposed. For example, free-radical curable resin systems have been proposed. These systems generally consist of one or more (meth)acrylate compounds (or other free-radically polymerizable organic compounds) along with a free-radical photoinitiator for radical generation. While these systems tend to be low-viscosity and fast-curing, they are known to produce brittle parts that shrink after cure and possess inferior short- and long-term mechanical properties. They are therefore unsuitable for a wide range of stereolithography applications, including use in creating molds for dental aligners.

Another type of resin system potentially suitable for this purpose is a so-called "hybrid cure" type system that comprises (i) epoxy resins or other types of cationically polymerizable compounds; (ii) a cationic polymerization initiator; (iii) acrylate resins or other types of free-radically polymerizable compounds; and (iv) a free radical polymerization initiator.

It is well known in the field of liquid radiation curable resins that hybrid liquid radiation curable resins produce cured three-dimensional articles with the most desirable combination of mechanical properties. A hybrid liquid radiation curable resin is a liquid radiation curable resin that comprises both free radical and cationic polymerizable components and photoinitiators. It is also well known that the cationically polymerizable components of a liquid radiation curable resin primarily contribute to the desirable combination of mechanical properties in a cured three-dimensional article. However, the cationically polymerizable components of a liquid radiation curable resin polymerize at a much slower rate than the free-radically polymerizable components. Consequently, the mechanical properties of the cured three-dimensional article develop over time, long after the initial cure of the hybrid liquid radiation curable resin. Furthermore, many cationically polymerizable components substantially increase the initial viscosity of the radiation curable resin with which they are associated. Also, several cationically polymerizable components are reactive to ambient heat, light, and humidity conditions, and engage in a partial polymerization at unwanted times, thereby increasing the viscosity of the liquid radiation resin with which they are associated over time. The nature and concentration of the various reagents associated with a hybrid cure system is therefore of utmost importance when crafting a resin suitable for specialized applications.

One specific class of hybrid-cure systems suggested for use in stereolithographic resins and other radiation-curable resins include those containing one or more oxetane components. Several references have suggested the use of an oxetane as either a cationically polymerizing organic substance or as a reactive modifier component for such resins, including the following:

U.S. Pat. Nos. 5,434,196 and 5,525,645 (Ohkawa et al.) relate to resin compositions for optical molding which comprises (A) an actinic radiation-curable and cationically polymerizable organic substance and (B) an actinic radiation-sensitive initiator for cationic polymerization.

U.S. Pat. No. 5,674,922 (Igarashi et al.) discusses active energy beam-curable resin compositions which comprise (A) at least one oxetane compound (B) at least one epoxide compound and (C) at least one cationic initiator.

U.S. Pat. No. 5,981,616 (Yamamura et al.) discusses photo curable resin compositions that contain (A) an oxetane compound (B) one or more selected epoxy compounds and (C) a cationic photo-initiator.

U.S. Pat. No. 6,368,769 (Ohkawa et al.) discusses a stereolithographic resin composition that may include mixtures of the following: (A) cationically polymerizable organic substance that could be a mixture of an epoxy compound and an oxetane compound (3-ethyl-3-hydroxy methyloxetane is mentioned as an oxetane compound); (B) selected cationic photo-initiator; (C) radically polymerizable organic substance such as a polyacrylate; (D) radical photo-initiators; and (E) optional organic compounds having two or more hydroxyl groups per molecule (e.g., polyethers).

U.S. Pat. No. 6,413,696 (Pang et al.) discusses liquid, radiation-curable resin compositions that contain (A) 55-90% by weight of at least one solid or liquid actinic radiation-curable and cationically polymerizable organic substance (these may include oxetane compounds, see column 6, lines 42 to 54); (B) 0.05 to 10% by weight of an actinic radiation-sensitive initiator for cationic polymerization; (C) 5% to 25% by weight of an actinic radiation-curable and radical-polymerizable organic substance; (D) 0.02 to 10% by weight of an actinic radiation-sensitive initiator for radical polymerization; and (E) 0.5 to about 40 percent by weight of at least one solid or liquid cationically reactive modifier-flexibilizer, wherein the reactive modifier-flexibilizer is a reactive epoxy modifier, reactive vinylether modifier, reactive oxetane modifier, or mixtures thereof, and wherein the reactive modifier-flexibilizer contains at least one chain extension segment with a molecular weight of at least about 100 and not more than 2,000, wherein component (A) comprises at least one glycidylether of a polyhydric aliphatic, alicyclic or aromatic alcohol having at least three epoxy groups with epoxy equivalent weight between 90 and 800 g/equivalent and at least one solid or liquid alicyclic epoxide with epoxy equivalent weight between 80 and 330 having at least two epoxy groups with a monomer purity of at least about 80% by weight, or mixtures thereof.

European Patent No. 0848294 B (DSM N.V.; Japan Synthetic Rubber Col, LTD. and Japan Fiber Coatings, Ltd.) discusses a process for photo-fabricating a three-dimensional object by selectively curing a photo-curable resin composition comprising an (A) oxetane compound, (B) an epoxy compound and (C) a cationic photo-initiator wherein the oxetane compound (A) is either a compound comprising two or more oxetane rings or a specifically defined oxetane compound.

Japanese Published Patent Application (Kokai) No. 1-0158385 (Asahi Denka Kogyo KK) discusses a resin composition for optically three-dimensional molding containing a cationic polymerizable organic material containing an oxetane ring in its molecule.

U.S. Pat. No. 7,183,040 (Thies et al.) discusses a radiation curable resin composition comprising relative to the total weight of the resin composition (A) 0-29 wt % of a cationically curable component having a linking aliphatic ester group, (B) 10-85 wt % of an epoxygroup containing component other than A, (C) 1-50 wt % of an oxetanegroup containing component, (D) 1-25 wt % of a multifunctional acrylate and a radical photoinitiator and a cationic photoinitiator.

While one or more of the aforementioned references discusses resin compositions optimized for low-viscosity, ideal mechanical properties, or dimensional stability, none provide a resin suited for the full gamut of properties specifically required by the dental aligner manufacturing industry.

Additionally, several references discuss the use of a polyol or hydroxy containing component in a radiation curable resin composition, including the following:

U.S. Pat. No. 6,127,085 (Yamamura et al.) discusses a photo-curable resin composition comprising (A) a specific epoxy compound having a cyclohexane oxide; (B) a cationic photo-initiator; (C) a specific ethylenically unsaturated monomer; (D) a radical photo-initiator; and (E) a polyol.

U.S. Pat. No. 6,136,497 (Melisaris et al.) discusses a method for producing three-dimensional shaped articles with a radiation-curable resin composition containing (A) 20-90% by weight of cationically polymerizing compounds; (B) 0.05-12% by weight of cationic initiator; and (C) 0.5-60% by weight of at least selected cationic reactive modifiers.

U.S. Pat. No. 6,379,866 (Lawton et al.) discusses a photosensitive resin composition comprising (A) 30-70% by weight of a cycloaliphatic diepoxide; (B) 5-35% by weight of an acrylic material selected from aromatic acrylic material or combinations thereof; (C) 10-39% by weight of an aliphatic polycarbonate diol or polytetrahydrofuran polyether polyol; (D) at least one cationic photoinitiator; and (E) at least one free-radical photoinitiator.

U.S. Pat. No. 7,232,850 (Fong et al.) discusses a photocurable resin composition comprising cationically curable compound, an acrylate-containing compound; a hydroxyl-containing compound; a cationic photoinitiator; and a free radical photoinitiator; wherein said resin composition has less than 0.54 equivalents of cationically curable groups, less than 0.10 equivalents of acrylate groups and less than 0.10 equivalents of hydroxyl groups per 100 grams of said resin composition.

U.S. Pat. No. 5,476,748 (Steinmann et al.) discusses an invention of photosensitive resin compositions comprising: (A) from 40 to 80% by weight of at least one liquid epoxy resin having an epoxy functionality of equal to or greater than 2, (B) from 0.1 to 10% by weight of at least one cationic photoinitiator for component (A), (C) from 5 to 40% by weight of at least one liquid cycloaliphatic or aromatic diacrylate, (D) from 0 to 15% by weight of at least one liquid poly(meth-)acrylate having a (meth-)acrylate functionality of greater than 2, the proportion of component (D) constituting a maximum of 50% by weight of the total (meth-)acrylate content, (E) from 0.1 to 10% by weight of at least one radical photoinitiator for component (C) and, where appropriate, (D) and (F) from 5 to 40% by weight of at least one OH-terminated polyether, polyester or polyurethane, which are especially suitable, for example, for the manufacture of photopolymerized layers, especially of three-dimensional objects.

U.S. Pat. No. 8,501,033 (Southwell et al.) discusses a liquid radiation curable resin capable of curing into a solid upon irradiation comprising: (A) from about 0 to about 12 wt % of a cycloaliphatic epoxide having a linking ester group; (B) from about 30 to about 65 wt % of one or more epoxy functional components other than A; (C) from about 10 to about 30 wt % of one or more oxetanes; (D) from about 1 to about 10 wt % of one or more polyols; (E) from about 2 to about 20 wt % of one or more radically curable (meth) acrylate components; (F) from about 2 to about 12 wt % of one or more impact modifiers; (G) from about 0.1 to about 8 wt % of one or more free radical photoinitiators; and (H) from about 0.1 to about 8 wt % of one or more cationic photoinitiators; wherein the liquid radiation curable resin has a viscosity at 30° C. of from about 600 cps to about 1300 cps.

U.S. No. 2008/0103226 (Xu et al.) discusses a radiation curable resin composition comprising from about 50 wt % to about 70 wt % of a cycloaliphatic diepoxide, from about 5 wt % to about 15 wt % of a polyol, from about 5 wt % to about 15 wt % of an oxetane, from about 10 wt % to about 20 wt % of an aromatic diacrylate, a radical photoinitiator and a cationic photoinitiator. The invention further relates to a process for making a three dimensional article from the resin composition of the invention, the three-dimensional article itself and to the use of the resin composition of the invention.

US 2004/0137368 (Steinmann) discusses a liquid radiation curable resin composition that comprises cationically polymerizable substances, radically polymerizable substances, a hydroxyl functional component and at least one hydroxyl-functional oxetane compound.

The aforementioned references' requirement that a polyol component be used reduces the disclosed resin compositions' usefulness in dental aligner mold applications. Furthermore, none of these references, nor any other known liquid radiation curable resin composition for additive manufacturing, heretofore exists which provides the requisite balance of glass transition temperature (Tg), dimensional precision, viscosity, stability, and long-term mechanical integrity for optimum suitability in dental aligner mold fabrication applications.

The foregoing shows that there is a long-felt, but unmet need to provide a liquid radiation curable resin composition of sufficiently high strength, high precision, low-viscosity, high viscosity stability, high dimensional stability, and high long-term mechanical integrity to be ideally suited for producing three-dimensional molds having properties sufficient for dental aligner applications.

BRIEF SUMMARY OF THE INVENTION

The first aspect of the claimed invention is a liquid radiation curable resin composition comprising, relative to the total weight of the composition:
(a) from about 50 to about 80 wt % of an epoxy, further comprising:
  a cycloaliphatic epoxy component, and
  an epoxy component having an aromatic glycidyl ether group;
(b) from about 5 to about 30 wt % of an oxetane;
(c) a (meth)acrylate component;
(d) a cationic photoinitiator; and
(e) a free-radical photoinitiator;
wherein at least 25 wt % of the epoxy is the cycloaliphatic epoxy component; and
wherein the resin liquid radiation curable resin composition has a viscosity of between about 75 and about 300 cps at 30 degrees Celsius.

An alternative embodiment of the first aspect of the claimed invention is a liquid radiation curable resin composition comprising, relative to the total weight of the composition:

(a) from about 50 to about 80 wt % of an epoxy component, further comprising:
   a cycloaliphatic epoxy, and
   an epoxy having an aromatic glycidyl ether group;
(b) 5 to 30 wt % of an oxetane;
(c) a (meth)acrylate component;
(d) a cationic photoinitiator; and
(e) a free-radical photoinitiator;
wherein the ratio of the cycloaliphatic epoxy component to the epoxy component having an aromatic glycidyl ether group to the oxetane is from 1.5:1:1 to 5:2:1;
wherein the liquid radiation curable resin composition is substantially free of a polyol;
wherein the liquid radiation curable resin composition is substantially free of a stabilizer;
and wherein the liquid radiation curable resin composition has a viscosity of between 75 and 200 cps at 30° Celsius.

The second aspect of the claimed invention is a process for forming a dental aligner mold, comprising:
(1) placing a first liquid layer of a liquid radiation curable resin composition, thereby forming a surface, wherein the liquid radiation curable resin composition is as defined in claim 3;
(2) exposing the first liquid layer imagewise to actinic radiation to form an imaged cross-section, wherein the radiation is of sufficient intensity to cause substantial curing of the first liquid layer in the exposed areas, thereby forming a first cured layer;
(3) lowering the first cured layer in a direction substantially orthogonal to, and away from, the surface, thereby allowing a new layer of liquid radiation curable resin composition to freely flow over the first cured layer without a recoating operation;
(4) exposing said new layer from step (3) imagewise to actinic radiation to form an additional imaged cross-section, wherein the radiation is of sufficient intensity to cause substantial curing of the new layer in the exposed areas and to cause adhesion to the first cured layer; and
(5) repeating steps (3) and (4) a sufficient number of times in order to build up a dental aligner mold.

An alternative embodiment of the second aspect of the claimed invention is the process of the second aspect of the claimed invention, further comprising the step of:
(6) vacuum forming a thermoplastic sheet over the dental aligner mold to form a dental aligner.

The third aspect of the claimed invention is the dental aligner mold created by the process according to the second aspect of the claimed invention.

DETAILED DESCRIPTION OF THE INVENTION

An embodiment of the claimed invention is a liquid radiation curable resin composition comprising, relative to the total weight of the composition:
(a) from about 50 to about 80 wt % of an epoxy, further comprising:
   a cycloaliphatic epoxy component, and
   an epoxy component having an aromatic glycidyl ether group;
(b) from about 5 to about 30 wt % of an oxetane;
(c) a (meth)acrylate component;
(d) a cationic photoinitiator; and
(e) a free-radical photoinitiator;

wherein at least 25 wt % of the epoxy is the cycloaliphatic epoxy component; and
wherein the resin liquid radiation curable resin composition has a viscosity of between about 75 and about 300 cps at 30 degrees Celsius.

Another embodiment of the claimed invention is a liquid radiation curable resin composition comprising, relative to the total weight of the composition:
(a) from about 50 to about 80 wt % of an epoxy component, further comprising:
   a cycloaliphatic epoxy, and
   an epoxy having an aromatic glycidyl ether group;
(b) 5 to 30 wt % of an oxetane;
(c) a (meth)acrylate component;
(d) a cationic photoinitiator; and
(e) a free-radical photoinitiator;
wherein the ratio of the cycloaliphatic epoxy component to the epoxy component having an aromatic glycidyl ether group to the oxetane is from 1.5:1:1 to 5:2:1;
wherein the liquid radiation curable resin composition is substantially free of a polyol;
wherein the liquid radiation curable resin composition is substantially free of a stabilizer;
and wherein the liquid radiation curable resin composition has a viscosity of between 75 and 200 cps at 30° Celsius.

Yet another embodiment of the claimed invention is a liquid radiation curable resin composition consisting essentially of, relative to the total weight of the resin composition:
(a) from about 50 to about 80 wt % of an epoxy component, further comprising:
   a cycloaliphatic epoxy, and
   an epoxy having an aromatic glycidyl ether group;
(b) from about 5 to about 30 wt % of an oxetane;
(c) a radically polymerizable component having at least 4 functional groups;
(d) a cationic photoinitiator; and
(e) a free-radical photoinitiator;
wherein the ratio by weight relative to the total resin composition of the cycloaliphatic epoxy component to the epoxy component having an aromatic glycidyl ether group to the oxetane component is from 1.5:1:1 to 5:2:1.

Cationically Polymerizable Component

In accordance with an embodiment, the liquid radiation curable resins for additive manufacturing of the invention comprise at least one cationically polymerizable component; that is a component which undergoes polymerization initiated by cations or in the presence of acid generators. The cationically polymerizable components may be monomers, oligomers, and/or polymers, and may contain aliphatic, aromatic, cycloaliphatic, arylaliphatic, heterocyclic moiety(ies), and any combination thereof. Suitable cyclic ether compounds can comprise cyclic ether groups as side groups or groups that form part of an alicyclic or heterocyclic ring system.

The cationic polymerizable component is selected from the group consisting of cyclic ether compounds, cyclic acetal compounds, cyclic thioethers compounds, spiro-orthoester compounds, cyclic lactone compounds, and vinyl ether compounds, and any combination thereof.

Suitable cationically polymerizable components include cyclic ether compounds such as epoxy compounds and oxetanes, cyclic lactone compounds, cyclic acetal compounds, cyclic thioether compounds, spiro orthoester compounds, and vinylether compounds. Specific examples of cationically polymerizable components include bisphenol A diglycidyl ether, bisphenol F diglycidyl ether, bisphenol S diglycidyl ether, brominated bisphenol A diglycidyl ether, brominated bisphenol F diglycidyl ether, brominated bisphenol S diglycidyl ether, epoxy novolac resins, hydrogenated bisphenol A diglycidyl ether, hydrogenated bisphenol F diglycidyl ether, hydrogenated bisphenol S diglycidyl ether, 3,4-epoxycyclohexylmethyl-3',4'-epoxycyclohexanecarboxylate, 2-(3,4-epoxycyclohexyl-5,5-spiro-3,4-epoxy)-cyclohexane-1,4-dioxane, bis(3,4-epoxycyclohexylmethyl)adipate, vinylcyclohexene oxide, 4-vinylepoxycyclohexane, vinylcyclohexene dioxide, limonene oxide, limonene dioxide, bis(3,4-epoxy-6-methylcyclohexylmethyl)adipate, 3,4-epoxy-6-methylcyclohexyl-3',4'-epoxy-6'-methylcyclohexanecarboxylate, ε-caprolactone-modified 3,4-epoxycyclohexylmethyl-3',4'-epoxycyclohexane carboxylates, trimethylcaprolactone-modified 3,4-epoxycyclohexylmethyl-3',4'-epoxycyclohexane carboxylates, β-methyl-δ-valerolactone-modified 3,4-epoxycyclohexcylmethyl-3',4'-epoxycyclohexane carboxylates, methylenebis(3,4-epoxycyclohexane), bicyclohexyl-3,3'-epoxide, bis(3,4-epoxycyclohexyl) with a linkage of —O—, —S—, —SO—, —SO$_2$—, —C(CH$_3$)$_2$—, —CBr$_2$—, —C(CBr$_3$)$_2$—, —C(CF$_3$)$_2$—, —C(CCl$_3$)$_2$—, or —CH(C$_6$H$_5$)—, dicyclopentadiene diepoxide, di(3,4-epoxycyclohexylmethyl) ether of ethylene glycol, ethylenebis(3,4-epoxycyclohexanecarboxylate), epoxyhexahydrodioctylphthalate, epoxyhexahydro-di-2-ethylhexyl phthalate, 1,4-butanediol diglycidyl ether, 1,6-hexanediol diglycidyl ether, neopentylglycol diglycidyl ether, glycerol triglycidyl ether, trimethylolpropane triglycidyl ether, polyethylene glycol diglycidyl ether, polypropylene glycol diglycidyl ether, diglycidyl esters of aliphatic long-chain dibasic acids, monoglycidyl ethers of aliphatic higher alcohols, monoglycidyl ethers of phenol, cresol, butyl phenol, or polyether alcohols obtained by the addition of alkylene oxide to these compounds, glycidyl esters of higher fatty acids, epoxidated soybean oil, epoxybutylstearic acid, epoxyoctylstearic acid, epoxidated linseed oil, epoxidated polybutadiene, 1,4-bis[(3-ethyl-3-oxetanylmethoxy)methyl]benzene, 3-ethyl-3-hydroxymethyloxetane, 3-ethyl-3-(3-hydroxypropyl)oxymethyloxetane, 3-ethyl-3-(4-hydroxybutyl)oxymethyloxetane, 3-ethyl-3-(5-hydroxypentyl)oxymethyloxetane, 3-ethyl-3-phenoxymethyloxetane, bis((1-ethyl(3-oxetanyl))methyl)ether, 3-ethyl-3-((2-ethylhexyloxy)methyl)oxetane, 3-ethyl-((triethoxysilylpropoxymethyl)oxetane, 3-(meth)allyloxymethyl-3-ethyloxetane, 3-hydroxymethyl-3-ethyloxetane, (3-ethyl-3-oxetanylmethoxy)methylbenzene, 4-fluoro-[1-(3-ethyl-3-oxetanylmethoxy)methyl]benzene, 4-methoxy-[1-(3-ethyl-3-oxetanylmethoxy)methyl]-benzene, [1-(3-ethyl-3-oxetanylmethoxy)ethyl]phenyl ether, isobutoxymethyl(3-ethyl-3-oxetanylmethyl)ether, 2-ethylhexyl(3-ethyl-3-oxetanylmethyl)ether, ethyldiethylene glycol(3-ethyl-3-oxetanylmethyl)ether, dicyclopentadiene (3-ethyl-3-oxetanylmethyl)ether, dicyclopentenyloxyethyl (3-ethyl-3-oxetanylmethyl)ether, dicyclopentenyl(3-ethyl-3-oxetanylmethyl)ether, tetrahydrofurfuyl(3-ethyl-3-oxetanylmethyl)ether, 2-hydroxyethyl(3-ethyl-3-oxetanylmethyl) ether, 2-hydroxypropyl(3-ethyl-3-oxetanylmethyl)ether, and any combination thereof.

The cationically polymerizable component may optionally also contain polyfunctional materials including dendritic polymers such as dendrimers, linear dendritic polymers, dendrigraft polymers, hyperbranched polymers, star branched polymers, and hypergraft polymers with epoxy or oxetane functional groups. The dendritic polymers may contain one type of polymerizable functional group or different types of polymerizable functional groups, for example, epoxy and oxetane functions.

In an embodiment, the epoxide is 3,4-epoxycyclohexylmethyl-3',4-epoxycyclohexanecarboxylate (available as CELLOXIDE™ 2021P from Daicel Chemical, or as CYRACURE™ UVR-6105 from Dow Chemical), hydrogenated bisphenol A-epichlorohydrin based epoxy resin (available as EPON™ 1510 from Momentive), 1,4-cyclohexanedimethanol diglycidyl ether (available as HELOXY™ 107 from Momentive), a hydrogenated bisphenol A diglycidyl ether (available as EPON™ 825 from Momentive) a mixture of dicyclohexyl diepoxide and nanosilica (available as NANOPDX™), and any combination thereof.

The above-mentioned cationically polymerizable compounds can be used singly or in combination of two or more thereof.

The inventor has surprisingly discovered that desirable viscosity, viscosity stability, and dimensional stability can be achieved with a large amount of certain cationically polymerizable components present in certain amounts and ratios. The liquid radiation curable resin for additive manufacturing can therefore include suitable amounts of the cationic polymerizable component, for example, in certain embodiments, in an amount from about 40 to about 90% by weight of the resin composition, in further embodiments from about 50 to about 85 wt % of the resin composition, in further embodiments from about 50 to about 80 wt % of the resin composition, in further embodiments from about 60 to about 85 wt % of the resin composition, and in further embodiments from about 65 to about 80 wt % of the resin composition.

In embodiments of the invention, the cationic polymerizable component further comprises at least two different epoxy components. In a specific embodiment, the cationic polymerizable component includes a cycloaliphatic epoxy, for example, a cycloaliphatic epoxy with 2 or more than 2 epoxy groups. In another specific embodiment, the cationic polymerizable component includes an epoxy having an aromatic glycidyl ether group with 2 (difunctional) or more than 2 (polyfunctional) epoxy groups.

In yet another specific embodiment, the cationic polymerizable component includes both a cycloaliphatic epoxy component and an epoxy component with a di- or polyfunctional aromatic glycidyl ether group. The inventor has found that several performance characteristics such as low viscosity and Young's modulus, which are important to, among others, dental aligner mold applications, are particularly enhanced when the cycloaliphatic epoxy represents the majority of total epoxides present in the resin composition. That is, the cycloaliphatic epoxy component is present in an amount of greater than 50% by weight relative to the total amount of epoxides present in the resin composition. This unexpectedly occurs without a sacrifice in glass transition temperature (Tg) after thermal cure of aligner molds. In a particularly preferred embodiment, the ratio of cycloaliphatic epoxy components to epoxy components having an aromatic glycidyl ether group is at between 1:1 to 1.5:1. In another preferred embodiment, the ratio of cycloaliphatic epoxy components to epoxy components having an aromatic glycidyl ether group is at least 1.5:1. In another preferred embodiment, this ratio is between 1.5:1 to 2:1. In another preferred embodiment, this ratio is from 2.5:1 to 2:1. In another preferred embodiment, this ratio is greater than 2.5:1.

In other embodiments of the invention, the cationic polymerizable component also comprises an oxetane component. In a specific embodiment, the cationic polymerizable component includes an oxetane, for example, an oxetane containing 1, 2 or more than 2 oxetane groups. The inventor has found that oxetanes, particularly monofunctional oxetanes, tend to reduce the viscosity of the formulation as they increase in concentration. However, they also create a more linear network which significantly reduces both the Young's modulus and the Tg after thermal post processing of dental aligner molds. In an embodiment, therefore, the oxetane component is present in a suitable amount from about 5 to about 30 wt % of the resin composition. In another embodiment, the oxetane component is present in an amount from about 10 to about 25 wt % of the resin composition, and in yet another embodiment, the oxetane component is present in an amount from 20 to about 30 wt % of the resin composition.

During the development of the resin compositions disclosed herein, it was noted that substantial changes to one or more of the glass transition temperatures (Tg), dimensional precision, viscosity, viscosity stability, dimensional stability, and long-term mechanical strength by the liquid solid imaging process could be effectuated by only slight alterations in component concentrations and ratios of concentration. Specifically, the inventor has surprisingly found that when certain ratios of the aforementioned cationically polymerizable components are present, the resin composition exhibits superior performance in terms of viscosity, viscosity stability, post-cured glass transition temperature (Tg), dimensional stability, and long-term mechanical strength after humidity exposure. These properties are especially valuable in stereolithography applications wherein finished parts made from the liquid radiation curable resins are used as molds to create, for example, dental aligners. The superior performance of resins in such applications are particularly pronounced when the ratio of cycloaliphatic epoxy to epoxy containing an aromatic glycidyl ether group to oxetane is from 1.5:1:1 to 5:2:1. These results are particularly surprising in light of the phenomenon well-known in the art that resin compositions containing high amounts of cycloaliphatic epoxies with linking ester groups and oxetanes generally tend to be extremely moisture sensitive.

In accordance with an embodiment, the liquid radiation curable resin composition for additive manufacturing contains a component that is polymerizable by both free-radical polymerization and cationic polymerization. An example of such a polymerizable component is a vinyloxy compound, for example, one selected from the group consisting of bis(4-vinyloxybutyl)isophthalate, tris(4-vinyloxybutyl)trimellitate, and combinations thereof. Other examples of such a polymerizable component include those containing an acrylate and an epoxy group, or an acrylate and an oxetane group, on a same molecule.

Radically Polymerizable Component

In accordance with an embodiment of the invention, the liquid radiation curable resin for additive manufacturing of the invention comprises at least one free-radical polymerizable component, that is, a component which undergoes polymerization initiated by free radicals. The free-radical polymerizable components are monomers, oligomers, and/or polymers; they are monofunctional or polyfunctional materials, i.e., have 1, 2, 3, 4, 5, 6, 7, 8, 9, 10 . . . 20 . . . 30 . . . 40 . . . 50 . . . 100, or more functional groups that can polymerize by free radical initiation, may contain aliphatic, aromatic, cycloaliphatic, arylaliphatic, heterocyclic moiety (ies), or any combination thereof. Examples of polyfunctional materials include dendritic polymers such as dendrimers, linear dendritic polymers, dendrigraft polymers, hyperbranched polymers, star branched polymers, and hypergraft polymers; see, e.g., US 2009/0093564 A1. The dendritic polymers may contain one type of polymerizable functional group or different types of polymerizable functional groups, for example, acrylates and methacrylate functions.

Examples of free-radical polymerizable components include acrylates and methacrylates such as isobornyl (meth)acrylate, bornyl (meth)acrylate, tricyclodecanyl (meth)acrylate, dicyclopentanyl (meth)acrylate, dicyclopentenyl (meth)acrylate, cyclohexyl (meth)acrylate, benzyl (meth)acrylate, 4-butylcyclohexyl (meth)acrylate, acryloyl morpholine, (meth)acrylic acid, 2-hydroxyethyl (meth)acrylate, 2-hydroxypropyl (meth)acrylate, 2-hydroxybutyl (meth)acrylate, methyl (meth)acrylate, ethyl (meth)acrylate, propyl (meth)acrylate, isopropyl (meth)acrylate, butyl (meth)acrylate, amyl (meth)acrylate, isobutyl (meth)acrylate, t-butyl (meth)acrylate, pentyl (meth)acrylate, caprolactone acrylate, isoamyl (meth)acrylate, hexyl (meth)acrylate, heptyl (meth)acrylate, octyl (meth)acrylate, isooctyl (meth)acrylate, 2-ethylhexyl (meth)acrylate, nonyl (meth)acrylate, decyl (meth)acrylate, isodecyl (meth)acrylate, tridecyl (meth)acrylate, undecyl (meth)acrylate, lauryl (meth)acrylate, stearyl (meth)acrylate, isostearyl (meth)acrylate, tetrahydrofurfuryl (meth)acrylate, butoxyethyl (meth)acrylate, ethoxydiethylene glycol (meth)acrylate, benzyl (meth)acrylate, phenoxyethyl (meth)acrylate, polyethylene glycol mono (meth)acrylate, polypropylene glycol mono(meth)acrylate, methoxyethylene glycol (meth)acrylate, ethoxyethyl (meth)acrylate, methoxypolyethylene glycol (meth)acrylate, methoxypolypropylene glycol (meth)acrylate, diacetone (meth)acrylamide, beta-carboxyethyl (meth)acrylate, phthalic acid (meth)acrylate, dimethylaminoethyl (meth)acrylate, diethylaminoethyl (meth)acrylate, butylcarbamylethyl (meth)acrylate, n-isopropyl (meth)acrylamide fluorinated (meth)acrylate, 7-amino-3,7-dimethyloctyl (meth)acrylate.

Examples of polyfunctional free-radical polymerizable components include those with (meth)acryloyl groups such as trimethylolpropane tri(meth)acrylate, pentaerythritol (meth)acrylate, ethylene glycol di(meth)acrylate, bisphenol A diglycidyl ether di(meth)acrylate, dicyclopentadiene dimethanol di(meth)acrylate, [2-[1,1-dimethyl-2-[(1-oxoallyl)oxy]ethyl]-5-ethyl-1,3-dioxan-5-yl]methyl acrylate; 3,9-bis(1,1-dimethyl-2-hydroxyethyl)-2,4,8,10-tetraoxaspiro[5.5]undecane di(meth)acrylate; dipentaerythritol monohydroxypenta(meth)acrylate, propoxylated trimethylolpropane tri(meth)acrylate, propoxylated neopentyl glycol di(meth)acrylate, tetraethylene glycol di(meth)acrylate, polyethylene glycol di(meth)acrylate, 1,4-butanediol di(meth)acrylate, 1,6-hexanediol di(meth)acrylate, neopentyl glycol di(meth)acrylate, polybutanediol di(meth)acrylate, tripropyleneglycol di(meth)acrylate, glycerol tri(meth)acrylate, phosphoric acid mono- and di(meth)acrylates, $C_7$-$C_{20}$ alkyl di(meth)acrylates, tris(2-hydroxyethyl)isocyanurate tri (meth)acrylate, tris(2-hydroxyethyl)isocyanurate di(meth)acrylate, pentaerythritol tri(meth)acrylate, pentaerythritol tetra(meth)acrylate, dipentaerythritol hexa(meth)crylate, tricyclodecane diyl dimethyl di(meth)acrylate and alkoxylated versions (e.g., ethoxylated and/or propoxylated) of any of the preceding monomers, and also di(meth)acrylate of a diol which is an ethylene oxide or propylene oxide adduct to bisphenol A, di(meth)acrylate of a diol which is an ethylene oxide or propylene oxide adduct to hydrogenated bisphenol A, epoxy (meth)acrylate which is a (meth)acrylate adduct to bisphenol A of diglycidyl ether, diacrylate of polyoxyalkylated bisphenol A, and triethylene glycol divinyl ether, and adducts of hydroxyethyl acrylate.

In accordance with an embodiment, the radically polymerizable component is a polyfunctional (meth)acrylate. The polyfunctional (meth)acrylates may include all methacryloyl groups, all acryloyl groups, or any combination of methacryloyl and acryloyl groups. In an embodiment, the free-radical polymerizable component is selected from the group consisting of bisphenol A diglycidyl ether di(meth)acrylate, ethoxylated or propoxylated bisphenol A or bisphenol F di(meth)acrylate, dicyclopentadiene dimethanol di(meth)acrylate, [2-[1,1-dimethyl-2-[(1-oxoallyl)oxy]ethyl]-5-ethyl-1,3-dioxan-5-yl]methyl acrylate, dipentaerythritol monohydroxypenta(meth)acrylate, dipentaerythritol penta(meth)acrylate, dipentaerythritol hexa(meth)crylate, propoxylated trimethylolpropane tri(meth)acrylate, and propoxylated neopentyl glycol di(meth)acrylate, and any combination thereof.

In a preferred embodiment, the polyfunctional (meth)acrylate has more than 2, more preferably more than 3, and more preferably greater than 4 functional groups.

In another preferred embodiment, the radically polymerizable component consists exclusively of a single polyfunctional (meth)acrylate component. In further embodiments, the exclusive radically polymerizable component is tetra-functional, in further embodiments, the exclusive radically polymerizable component is penta-functional, and in further embodiments, the exclusive radically polymerizable component is hexa-functional. The inventor has surprisingly found that use of a single polyfunctional (meth)acrylate having more than 3 functional groups, when used in combination with certain other components described herein, enables good green strength without a significant sacrifice in viscosity and viscosity stability of the associated liquid radiation curable resin composition.

In another embodiment, the free-radical polymerizable component is selected from the group consisting of bisphenol A diglycidyl ether diacrylate, dicyclopentadiene dimethanol diacrylate, [2-[1,1-dimethyl-2-[(1-oxoallyl)oxy]ethyl]-5-ethyl-1,3-dioxan-5-yl]methyl acrylate, dipentaerythritol monohydroxypentaacrylate, propoxylated trimethylolpropane triacrylate, and propoxylated neopentyl glycol diacrylate, and any combination thereof.

In specific embodiments, the liquid radiation curable resins for additive manufacturing of the invention include one or more of bisphenol A diglycidyl ether di(meth)acrylate, dicyclopentadiene dimethanol di(meth)acrylate, dipentaerythritol monohydroxypenta(meth)acrylate, propoxylated trimethylolpropane tri(meth)acrylate, and/or propoxylated neopentyl glycol di(meth)acrylate, and more specifically one or more of bisphenol A diglycidyl ether diacrylate, dicyclopentadiene dimethanol diacrylate, dipentaerythritol pentaacrylate, propoxylated trimethylolpropane triacrylate, and/or propoxylated neopentyl glycol diacrylate.

The liquid radiation curable resin for additive manufacturing can include any suitable amount of the free-radical polymerizable component, for example, in certain embodiments, in an amount up to about 40 wt % of the resin composition, in certain embodiments, from about 2 to about 40 wt % of the resin composition, in other embodiments from about 10 to about 40 wt %, and in further embodiments from about 10 to about 25 wt % of the resin composition. Furthermore, in certain embodiments, the ratio by weight relative to the total resin composition of radically polymerizable components to cationically polymerizable components is from about 1:3 to about 1:5, in other embodiments from about 1:5 to about 1:7, and in other embodiments from 1:7 to about 1:10.

Hydroxy Functional Components

Most of the known liquid radiation curable resin compositions for additive manufacturing use hydroxy-functional compounds to enhance the properties of the parts made from the resin compositions. It has been previously asserted, in U.S. Pat. No. 7,183,040, that hydroxy functional compounds that have no other cationically polymerizable functional group like an epoxy, oxetane or acrylate group, are not needed in liquid radiation curable resin compositions to obtain parts via stereolithography which have excellent mechanical properties.

The inventor has now surprisingly found that the substantial absence of hydroxy-functional compounds, including polyols, when coupled with the amount and ratio of cationically curable components described above, actually significantly improves properties desirable in stereolithography applications wherein finished parts made from the liquid radiation curable resins are optimally suitable for use as molds to create dental aligners. As previously noted, consistent with the unpredictable nature of the chemical arts, subtle changes in the ratios and or compositional amounts can lead to drastic differences in the properties of a cured component. The inventor has surprisingly found that liquid radiation curable resin compositions substantially devoid of hydroxy-functional compounds exhibit performance characteristics especially suitable for such applications when the ratio of cycloaliphatic epoxy to epoxy containing an aromatic glycidyl ether group to oxetane is from 1.5:1:1 to 5:2:1. In formulating such resin compositions, the inventor has filled a long-felt but unsolved need of a liquid radiation curable resin composition for use in producing dental aligner molds via stereolithography of sufficiently low viscosity and high viscosity stability to obviate the need for a recoating operation, all while providing the basis for finished components mechanical properties ideally suited for dental aligner mold fabrication applications. Particularly surprising is the discovery that liquid radiation curable resin compositions of the present invention substantially lacking a polyol exhibit improved dimensional and thermal stability as against comparable known prior-art resins having such polyols. It has been found that the inclusion of a polyol in liquid radiation curable resin compositions of the present invention tend to worsen desirable properties of both the liquid radiation curable resin composition, and the cured parts from which the resin is formed, including, but not necessarily limited to: stiffness, Tg, and hydrolytic stability. In a preferred embodiment, therefore, the resin composition comprises less than 5% of a polyol, more preferably, less than 4% of a polyol, even more preferably less than 3% of a polyol, even more preferably less than 2% of a polyol, even more preferably less than 1% of a polyol, even more preferably less than 0.5% of a polyol, and most preferably less than 0.2% of a polyol (herein considered to be "substantially free" of a polyol).

In other aspects of the invention, the resin composition may nonetheless contain a hydroxy-functional component. The hydroxyl-containing material which can be used in the present invention may be any suitable organic material having a hydroxyl functionality of at least 1. If present, the material is preferably substantially free of any groups which interfere with the curing reactions or which are thermally or photolytically unstable.

If present, any hydroxy group may be employed for the particular purpose. If present, the hydroxyl-containing material preferably contains one or more primary or secondary aliphatic hydroxyl. The hydroxyl group may be internal in the molecule or terminal. Monomers, oligomers or polymers can be used. The hydroxyl equivalent weight, i.e., the number average molecular weight divided by the number of hydroxyl groups, is preferably in the range of 31 to 5000.

Representative examples of hydroxyl-containing materials having a hydroxyl functionality of 1 include alkanols, monoalkyl ethers of polyoxyalkyleneglycols, mohoalkyl ethers of alkyleneglycols, and others, and combinations thereof.

Representative examples of monomeric polyhydroxy organic materials include alkylene and arylalkylene glycols and polyols, such as 1,2,4-butanetriol, 1,2,6-hexanetriol, 1,2,3-heptanetriol, 2,6-dimethyl-1,2,6-hexanetriol, (2R,3R)-(−)-2-benzyloxy-1,3,4-butanetriol, 1,2,3-hexanetriol, 1,2,3-butanetriol, 3-methyl-1,3,5-pentanetriol, 1,2,3-cyclohexanetriol, 1,3,5-cyclohexanetriol, 3,7,11,15-tetramethyl-1,2,3-hexadecanetriol, 2-hydroxymethyltetrahydropyran-3,4,5-triol, 2,2,4,4-tetramethyl-1,3-cyclobutanediol, 1,3-cyclopentanediol, trans-1,2-cyclooctanediol, 1,16-hexadecanediol, 3,6-dithia-1,8-octanediol, 2-butyne-1,4-diol, 1,3-propanediol, 1,4-butanediol, 1,5-pentanediol, 1,6-hexanediol, 1,7-heptanediol, 1,8-octanediol, 1,9-nonanediol, 1-phenyl-1,2-ethanediol, 1,2-cyclohexanediol, 1,5-decalindiol, 2,5-dimethyl-3-hexyne-2,5-diol, 2,7-dimethyl-3,5-octadiyne-2-7-diol, 2,3-butanediol, 1,4-cyclohexanedimethanol, and combinations thereof.

Representative examples of oligomeric and polymeric hydroxyl-containing materials include polyoxyethylene and polyoxypropylene glycols and triols of molecular weights from about 200 to about 10,000; polytetramethylene glycols of varying molecular weight; poly(oxyethylene-oxybutylene) random or block copolymers; copolymers containing pendant hydroxy groups formed by hydrolysis or partial hydrolysis of vinyl acetate copolymers, polyvinylacetal resins containing pendant hydroxyl groups; hydroxy-terminated polyesters and hydroxy-terminated polylactones; hydroxy-functionalized polyalkadienes, such as polybutadiene; aliphatic polycarbonate polyols, such as an aliphatic polycarbonate diol; and hydroxy-terminated polyethers, and combinations thereof.

If present, preferred hydroxyl-containing monomers include 1,4-cyclohexanedimethanol and aliphatic and cycloaliphatic monohydroxy alkanols. Such preferred hydroxyl-containing oligomers and polymers include hydroxyl and hydroxyl/epoxy functionalized polybutadiene, polycaprolactone diols and triols, ethylene/butylene polyols, and monohydroxyl functional monomers. Preferred examples of polyether polyols are polypropylene glycols of various molecular weights and glycerol propoxylate-B-ethoxylate triol. If present, especially preferred are linear and branched polytetrahydrofuran polyether polyols available in various molecular weights, such as in the range of 150-4000 g/mol, preferably in the range of 150-1500 g/mol, more preferably in the range of 150-750 g/mol.

If present, the resin composition preferably comprises, relative to the total weight of the resin composition, at most 10 wt % of one or more non-free radical polymerizable hydroxy-functional compounds, more preferably at most 5 wt %, and most preferably at most 2 wt %.

In embodiments, the liquid radiation curable resin for additive manufacturing of the present invention includes a photoinitiating system. The photoinitiating system can include a free-radical photoinitiator or a cationic photoinitiator. In accordance with an embodiment, the liquid radiation curable resin composition includes a photoinitiating system contains at least one photoinitiator having a cationic initiating function, and at least one photoinitiator having a free radical initiating function. Additionally, the photoinitiating system can include a photoinitiator that contains both free-radical initiating function and cationic initiating function on the same molecule. The photoinitiator is a compound that chemically changes due to the action of light or the synergy between the action of light and the electronic excitation of a sensitizing dye to produce at least one of a radical, an acid, and a base.

Cationic Photoinitiator

In accordance with an embodiment, the liquid radiation curable resin composition includes a cationic photoinitiator. The cationic photoinitiator initiates cationic ring-opening polymerization upon irradiation of light.

In an embodiment, any suitable cationic photoinitiator can be used, for example, those with cations selected from the group consisting of onium salts, halonium salts, iodosyl salts, selenium salts, sulfonium salts, sulfoxonium salts, diazonium salts, metallocene salts, isoquinolinium salts, phosphonium salts, arsonium salts, tropylium salts, dialkylphenacylsulfonium salts, thiopyrilium salts, diaryl iodonium salts, triaryl sulfonium salts, ferrocenes, di(cyclopentadienyliron)arene salt compounds, and pyridinium salts, and any combination thereof.

In another embodiment, the cation of the cationic photoinitiator is selected from the group consisting of aromatic diazonium salts, aromatic sulfonium salts, aromatic iodonium salts, metallocene based compounds, aromatic phosphonium salts, and any combination thereof. In another embodiment, the cation is a polymeric sulfonium salt, such as in U.S. Pat. No. 5,380,923 or U.S. Pat. No. 5,047,568, or other aromatic heteroatom-containing cations and naphthylsulfonium salts such as in U.S. Pat. No. 7,611,817, U.S. Pat. No. 7,230,122, US2011/0039205, US2009/0182172, U.S. Pat. No. 7,678,528, EP2308865, WO2010046240, or EP2218715. In another embodiment, the cationic photoinitiator is selected from the group consisting of triarylsulfonium salts, diaryliodonium salts, and metallocene based compounds, and any combination thereof. Onium salts, e.g., iodonium salts and sulfonium salts, and ferrocenium salts, have the advantage that they are generally more thermally stable.

In a particular embodiment, the cationic photoinitiator has an anion selected from the group consisting of $BF_4^-$, $AsF_6^-$, $SbF_6^-$, $PF_6^-$, $[B(CF_3)_4]^-$, $B(C_6F_5)_4^-$, $B[C_6H_3\text{-}3,5(CF_3)_2]_4^-$, $B(C_6H_4CF_3)_4^-$, $B(C_6H_3F_2)_4^-$, $B[C_6F_4\text{-}4(CF_3)]_4^-$, $Ga(C_6F_5)_4^-$, $[(C_6F_5)_3B\text{---}C_3H_3N_2\text{---}B(C_6F_5)_3]^-$, $[(C_6F_5)_3B\text{---}NH_2\text{---}B(C_6F_5)_3]^-$, tetrakis(3,5-difluoro-4-alkyloxyphenyl)borate, tetrakis(2,3,5,6-tetrafluoro-4-alkyloxyphenyl)borate, perfluoroalkylsulfonates, tris[(perfluoroalkyl)sulfonyl]methides, bis[(perfluoroalkyl)sulfonyl]imides, perfluoroalkylphosphates, tris(perfluoroalkyl)trifluorophosphates, bis(perfluoroalkyl)tetrafluorophosphates, tris(pentafluoroethyl)trifluorophosphates, and $(CH_6B_{11}Br_6)^-$, $(CH_6B_{11}Cl_6)^-$ and other halogenated carborane anions.

A survey of other onium salt initiators and/or metallocene salts can be found in "UV Curing, Science and Technology", (Editor S. P. Pappas, Technology Marketing Corp., 642 Westover Road, Stamford, Conn., U.S.A.) or "Chemistry & Technology of UV & EB Formulation for Coatings, Inks & Paints", Vol. 3 (edited by P. K. T. Oldring).

In an embodiment, the cationic photoinitiator has a cation selected from the group consisting of aromatic sulfonium salts, aromatic iodonium salts, and metallocene based compounds with at least an anion selected from the group consisting of $SbF_6^-$, $PF_6^-$, $B(C_6F_5)_4^-$, $[B(CF_3)_4]^-$, tetrakis(3,5-difluoro-4-methoxyphenyl)borate, perfluoroalkylsulfonates, perfluoroalkylphosphates, tris[(perfluoroalkyl)sulfonyl]methides, and $[(C_2F_5)_3PF_3]^-$.

Examples of cationic photoinitiators useful for curing at 300-475 nm, particularly at 365 nm UV light, without a sensitizer include 4-[4-(3-chlorobenzoyl)phenylthio]phenyl-bis(4-fluorophenyl)sulfonium hexafluoroantimonate, 4-[4-(3-chlorobenzoyl)phenylthio]phenylbis(4-fluorophenyl)sulfonium tetrakis(pentafluorophenyl)borate, 4-[4-(3-chlorobenzoyl)phenylthio]phenylbis(4-fluorophenyl)sulfonium tetrakis(3,5-difluoro-4-methyloxyphenyl)borate, 4-[4-(3-chlorobenzoyl)phenylthio]phenylbis(4-fluorophenyl)sulfonium tetrakis(2,3,5,6-tetrafluoro-4-methyloxyphenyl)borate, tris(4-(4-acetylphenyl)thiophenyl)sulfonium tetrakis(pentafluorophenyl)borate (Irgacure® PAG 290 from BASF), tris(4-(4-acetylphenyl)thiophenyl)sulfonium tris [(trifluoromethyl)sulfonyl]methide (Irgacure® GSID 26-1 from BASF), tris(4-(4-acetylphenyl)thiophenyl)sulfonium hexafluorophosphate (Irgacure® 270 from BASF), and HS-1 available from San-Apro Ltd.

Preferred cationic photoinitiators include, either alone or in a mixture: bis[4-diphenylsulfoniumphenyl]sulfide bishexafluoroantimonate; thiophenoxyphenylsulfonium hexafluoroantimonate (available as Chivacure 1176 from Chitec), tris(4-(4-acetylphenyl)thiophenyl)sulfonium tetrakis(pentafluorophenyl)borate (Irgacure® PAG 290 from BASF), tris(4-(4-acetylphenyl)thiophenyl)sulfonium tris [(trifluoromethyl)sulfonyl]methide (Irgacure® GSID 26-1 from BASF), and tris(4-(4-acetylphenyl)thiophenyl)sulfonium hexafluorophosphate (Irgacure® 270 from BASF), [4-(1-methylethyl)phenyl](4-methylphenyl) iodonium tetrakis(pentafluorophenyl)borate (available as Rhodorsil 2074 from Rhodia), 4-[4-(2-chlorobenzoyl)phenylthio]phenylbis(4-fluorophenyl)sulfonium hexafluoroantimonate (as SP-172 from Adeka), SP-300 from Adeka, and aromatic sulfonium salts with anions of $(PF_{6-m}(C_nF_{2n+1})_m)^-$ where m is an integer from 1 to 5, and n is an integer from 1 to 4 (available as CPI-200K or CPI-200S, which are monovalent sulfonium salts from San-Apro Ltd., TK-1 available from San-Apro Ltd., or HS-1 available from San-Apro Ltd.).

The liquid radiation curable resin composition can include any suitable amount of the cationic photoinitiator, for example, in certain embodiments, in an amount up to about 10% by weight of the resin composition, in certain embodiments, up to about 5% by weight of the resin composition, and in further embodiments from about 2% to about 10% by weight of the resin composition, and in other embodiments, from about 0.1% to about 5% by weight of the resin composition. In a further embodiment, the amount of cationic photoinitiator is from about 0.2 wt % to about 4 wt % of the total resin composition, and in other embodiments from about 0.5 wt % to about 3 wt %. In an embodiment, the above ranges are particularly suitable for use with epoxy monomers.

In some embodiments, depending on the wavelength of light used for curing the liquid radiation curable resin, it is desirable for the liquid radiation curable resin composition to include a photosensitizer. The term "photosensitizer" is used to refer to any substance that either increases the rate of photoinitiated polymerization or shifts the wavelength at which polymerization occurs; see textbook by G. Odian, Principles of Polymerization, 3$^{rd}$ Ed., 1991, page 222. A variety of compounds can be used as photosensitizers, including heterocyclic and fused-ring aromatic hydrocarbons, organic dyes, and aromatic ketones. Examples of photosensitizers include those selected from the group consisting of methanones, xanthenones, pyrenemethanols, anthracenes, pyrene, perylene, quinones, xanthones, thioxanthones, benzoyl esters, benzophenones, and any combination thereof. Particular examples of photosensitizers include those selected from the group consisting of [4-[(4-methylphenyl)thio]phenyl]phenyl-methanone, isopropyl-9H-thioxanthen-9-one, 1-pyrenemethanol, 9-(hydroxymethyl)anthracene, 9,10-diethoxyanthracene, 9,10-dimethoxyanthracene, 9,10-dipropoxyanthracene, 9,10-dibutyloxyanthracene, 9-anthracenemethanol acetate, 2-ethyl-9,10-dimethoxyanthracene, 2-methyl-9,10-dimethoxyanthracene, 2-t-butyl-9,10-dimethoxyanthracene, 2-ethyl-9,10-diethoxyanthracene and 2-methyl-9,10-diethoxyanthracene, anthracene, anthraquinones, 2-methylanthraquinone, 2-ethylanthraquinone, 2-tertbutylanthraquinone, 1-chloroanthraquinone, 2-amylanthraquinone, thioxanthones and xanthones, isopropyl thioxanthone, 2-chlorothioxanthone, 2,4-diethylthioxanthone, 1-chloro-4-propoxythioxanthone, methyl benzoyl formate (Darocur MBF from BASF), methyl-2-benzoyl benzoate (Chivacure OMB from Chitec), 4-benzoyl-4'-methyl diphenyl sulphide (Chivacure BMS from Chitec), 4,4'-bis(diethylamino) benzophenone (Chivacure EMK from Chitec), and any combination thereof.

The novel mixtures may also contain various photoinitiators of different sensitivity to radiation of emission lines with different wavelengths to obtain a better utilization of a UV light source. The use of known photoinitiators of different sensitivity to radiation of emission lines is well known in the art of stereo lithography, and may be selected in accordance with radiation sources of, for example, 351, nm 355 nm, 365 nm, 385 nm, and 405 nm. In this context it is advantageous for the various photoinitiators to be selected such, and employed in a concentration such, that equal optical absorption is produced with the emission lines used.

The liquid radiation curable resin composition can include any suitable amount of the photosensitizer, for example, in certain embodiments, in an amount up to about 10% by weight of the resin composition, in certain embodiments, up to about 5% by weight of the resin composition, and in further embodiments from about 0.05% to about 2% by weight of the resin composition.

Other Cationic Photoinitiators and Photosensitizers

In accordance with an embodiment, the liquid radiation curable resin for additive manufacturing includes a cationic photoinitiator in addition to an R-substituted aromatic thioether triaryl sulfonium tetrakis(pentafluorophenyl) borate cationic photoinitiator. Any suitable cationic photoinitiator can be used, for example, those selected from the group consisting of onium salts, halonium salts, iodosyl salts, selenium salts, sulfonium salts, sulfoxonium salts, diazonium salts, metallocene salts, isoquinolinium salts, phosphonium salts, arsonium salts, tropylium salts, dialkylphenacylsulfonium salts, thiopyrilium salts, diaryl iodonium salts, triaryl sulfonium salts, sulfonium antimonate salts, ferrocenes, di(cyclopentadienyliron)arene salt compounds, and pyridinium salts, and any combination thereof. Onium salts, e.g., iodonium salts, sulfonium salts and ferrocenes, have the advantage that they are thermally-stable. Thus, any residual photoinitiator does not continue to cure after the removal of the irradiating light. Cationic photoinitiators offer the advantage that they are not sensitive to oxygen present in the atmosphere.

Preferred mixtures of cationic photoinitiators include a mixture of: bis[4-diphenylsulfoniumphenyl]sulfide bishexafluoroantimonate; thiophenoxyphenylsulfonium hexafluoroantimonate (available as Chivacure 1176 from Chitec); tris(4-(4-acetylphenyl)thiophenyl)sulfonium tetrakis(pentafluorophenyl)borate (Irgacure PAG-290 or GSID4480-1 from Ciba/BASF), iodonium, [4-(1-methylethyl)phenyl](4-methylphenyl)-, tetrakis(pentafluorophenyl)borate (available as Rhodorsil 2074 from Rhodia), 4-[4-(2-chlorobenzoyl)phenylthio]phenylbis(4-fluorophenyl) sulfonium hexafluoroantimonate (as SP-172) and SP-300 (both available from Adeka).

In some embodiments it is desirable for the liquid radiation curable resin for additive manufacturing to include a photosensitizer. The term "photosensitizer" is used to refer to any substance that either increases the rate of photoinitiated polymerization or shifts the wavelength at which polymerization occurs; see textbook by G. Odian, Principles of Polymerization, 3$^{rd}$ Ed., 1991, page 222. Examples of photosensitizers include those selected from the group consisting of methanones, xanthenones, pyrenemethanols, anthracenes, pyrene, perylene, quinones, xanthones, thioxanthones, benzoyl esters, benzophenones, and any combination thereof. Particular examples of photosensitizers include those selected from the group consisting of [4-[(4-methylphenyl)thio]phenyl]phenyl-methanone, isopropyl-9H-thioxanthen-9-one, 1-pyrenemethanol, 9-(hydroxymethyl)anthracene, 9,10-diethoxyanthracene, 9,10-dimethoxyanthracene, 9,10-dipropoxyanthracene, 9,10-dibutyloxyanthracene, 9-anthracenemethanol acetate, 2-ethyl-9,10-dimethoxyanthracene, 2-methyl-9,10-dimethoxyanthracene, 2-t-butyl-9,10-dimethoxyanthracene, 2-ethyl-9,10-diethoxyanthracene and 2-methyl-9,10-diethoxyanthracene, anthracene, anthraquinones, 2-methylanthraquinone, 2-ethylanthraquinone, 2-tertbutylanthraquinone, 1-chloroanthraquinone, 2-amylanthraquinone, thioxanthones and xanthones, isopropyl thioxanthone, 2-chlorothioxanthone, 2,4-diethylthioxanthone, 1-chloro-4-propoxythioxanthone, methyl benzoyl formate, methyl-2-benzoyl benzoate, 4-benzoyl-4'-methyl diphenyl sulphide, 4,4'-bis(diethylamino) benzophenone, and any combination thereof.

Additionally, photosensitizers are useful in combination with photoinitiators in effecting cure with LED light sources emitting in the wavelength range of 300-475 nm. Examples of suitable photosensitizers include: anthraquinones, such as 2-methylanthraquinone, 2-ethylanthraquinone, 2-tertbutylanthraquinone, 1-chloroanthraquinone, and 2-amylanthraquinone, thioxanthones and xanthones, such as isopropyl thioxanthone, 2-chlorothioxanthone, 2,4-diethylthioxanthone, and 1-chloro-4-propoxythioxanthone, methyl benzoyl formate (Darocur MBF from Ciba), methyl-2-benzoyl benzoate (Chivacure OMB from Chitec), 4-benzoyl-4'-methyl diphenyl sulphide (Chivacure BMS from Chitec), 4,4'-bis(diethylamino) benzophenone (Chivacure EMK from Chitec).

In an embodiment, the photosensitizer is a fluorone, e.g., 5,7-diiodo-3-butoxy-6-fluorone, 5,7-diiodo-3-hydroxy-6-fluorone, 9-cyano-5,7-diiodo-3-hydroxy-6-fluorone, or a photosensitizer is

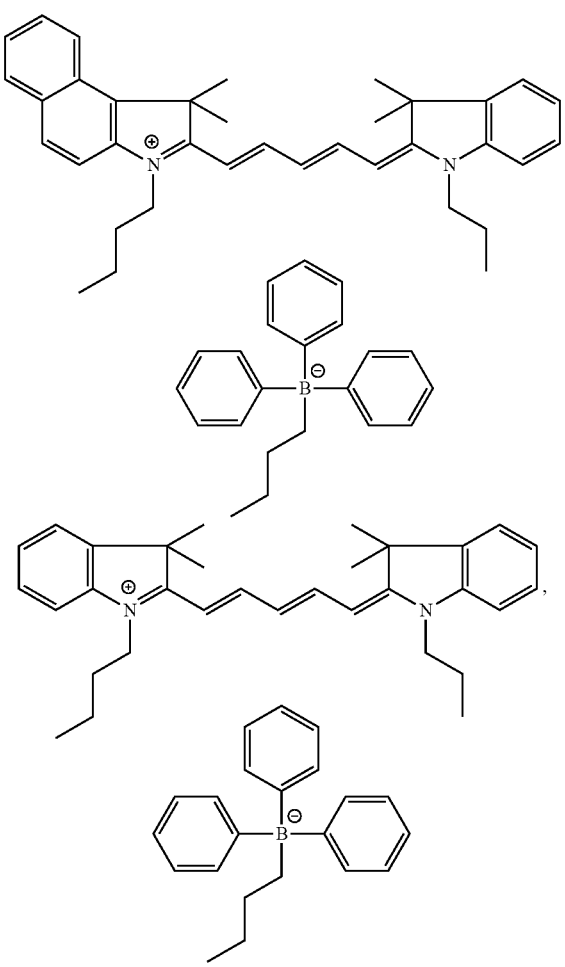

and any combination thereof.

The liquid radiation curable resin for additive manufacturing can include any suitable amount of the photosensitizer, for example, in certain embodiments, in an amount up to about 10% by weight of the resin composition, in certain embodiments, up to about 5% by weight of the resin composition, and in further embodiments from about 0.05% to about 2% by weight of the resin composition.

When photosensitizers are employed, other photoinitiators absorbing at shorter wavelengths can be used. Examples of such photoinitiators include: benzophenones, such as benzophenone, 4-methyl benzophenone, 2,4,6-trimethyl benzophenone, and dimethoxybenzophenone, and 1-hydroxyphenyl ketones, such as 1-hydroxycyclohexyl phenyl ketone, phenyl (1-hydroxyisopropyl)ketone, 2-hydroxy-1-[4-(2-hydroxyethoxyl)phenyl]-2-methyl-1-propanone, and 4-isopropylphenyl(1-hydroxyisopropyl)ketone, benzil dimethyl ketal, and oligo-[2-hydroxy-2-methyl-1-[4-(1-methylvinyl)phenyl]propanone] (Esacure KIP 150 from Lamberti). These photoinitiators when used in combination with a photosensitizer are suitable for use with LED light sources emitting at wavelengths from about 100 nm to about 300 nm.

A photosensitizer or co-initiator may be used to improve the activity of the cationic photoinitiator. It is for either increasing the rate of photoinitiated polymerization or shifting the wavelength at which polymerization occurs. The sensitizer used in combination with the above-mentioned cationic photoinitiator is not particularly limited. A variety of compounds can be used as photosensitizers, including heterocyclic and fused-ring aromatic hydrocarbons, organic dyes, and aromatic ketones. Examples of sensitizers include compounds disclosed by J. V. Crivello in *Advances in Polymer Science,* 62, 1 (1984), and by J. V. Crivello & K. Dietliker, "Photoinitiators for Cationic Polymerization" in Chemistry & technology of UV & EB formulation for coatings, inks & paints. Volume III, Photoinitiators for free radical and cationic polymerization. by K. Dietliker; [Ed. by P. K. T. Oldring], SITA Technology Ltd, London, 1991. Specific examples include polyaromatic hydrocarbons and their derivatives such as anthracene, pyrene, perylene and their derivatives, thioxanthones, α-hydroxyalkylphenones, 4-benzoyl-4'-methyldiphenyl sulfide, acridine orange, and benzoflavin.

The liquid radiation curable resin for additive manufacturing can include any suitable amount of the other cationic photoinitiator or photosensitizer, for example, in certain embodiments, in an amount an amount from 0.1 to 10 wt % of the resin composition, in certain embodiments, from about 1 to about 8 wt % of the resin composition, and in further embodiments from about 2 to about 6 wt % of the resin composition. In an embodiment, the above ranges are particularly suitable for use with epoxy monomers.

In accordance with an embodiment, the liquid radiation curable resin for additive manufacturing includes a photoinitiating system that is a photoinitiator having both cationic initiating function and free radical initiating function.

Free-Radical Photoinitiator

Typically, free radical photoinitiators are divided into those that form radicals by cleavage, known as "Norrish Type I" and those that form radicals by hydrogen abstraction, known as "Norrish type II". The Norrish type II photoinitiators require a hydrogen donor, which serves as the free radical source. As the initiation is based on a bimolecular reaction, the Norrrish type II photoinitiators are generally slower than Norrish type I photoinitiators which are based on the unimolecular formation of radicals. On the other hand, Norrish type II photoinitiators possess better optical absorption properties in the near-UV spectroscopic region. Photolysis of aromatic ketones, such as benzophenone, thioxanthones, benzil, and quinones, in the presence of hydrogen donors, such as alcohols, amines, or thiols leads to the formation of a radical produced from the carbonyl compound (ketyl-type radical) and another radical derived from the hydrogen donor. The photopolymerization of vinyl monomers is usually initiated by the radicals produced from the hydrogen donor. The ketyl radicals are usually not reactive toward vinyl monomers because of the steric hindrance and the delocalization of an unpaired electron.

To successfully formulate a liquid radiation curable resin for additive manufacturing, it is necessary to review the wavelength sensitivity of the photoinitiator(s) present in the resin composition to determine if they will be activated by the LED light chosen to provide the curing light.

In accordance with an embodiment, the liquid radiation curable resin for additive manufacturing includes at least one free radical photoinitiator, e.g., those selected from the group consisting of benzoylphosphine oxides, aryl ketones, benzophenones, hydroxylated ketones, 1-hydroxyphenyl ketones, ketals, metallocenes, and any combination thereof.

In an embodiment, the liquid radiation curable resin for additive manufacturing includes at least one free-radical photoinitiator selected from the group consisting of 2,4,6-trimethylbenzoyl diphenylphosphine oxide and 2,4,6-trimethylbenzoyl phenyl, ethoxy phosphine oxide, bis(2,4,6-trimethylbenzoyl)-phenylphosphineoxide, 2-methyl-1-[4-(methylthio)phenyl]-2-morpholinopropanone-1, 2-benzyl-2-(dimethylamino)-1-[4-(4-morpholinyl)phenyl]-1-butanone, 2-dimethylamino-2-(4-methyl-benzyl)-1-(4-morpholin-4-yl-phenyl)-butan-1-one, 4-benzoyl-4'-methyl diphenyl sulphide, 4,4'-bis(diethylamino) benzophenone, and 4,4'-bis(N,N'-dimethylamino) benzophenone (Michler's ketone), benzophenone, 4-methyl benzophenone, 2,4,6-trimethyl benzophenone, dimethoxybenzophenone, 1-hydroxycyclohexyl phenyl ketone, phenyl (1-hydroxyisopropyl)ketone, 2-hydroxy-1-[4-(2-hydroxyethoxy)phenyl]-2-methyl-1-propanone, 4-isopropylphenyl(1-hydroxyisopropyl)ketone, oligo-[2-hydroxy-2-methyl-1-[4-(1-methylvinyl)phenyl]propanone], camphorquinone, 4,4'-bis(diethylamino) benzophenone, benzil dimethyl ketal, bis (eta 5-2-4-cyclopentadien-1-yl) bis[2,6-difluoro-3-(1H-pyrrol-1-yl)phenyl]titanium, and any combination thereof.

For LED light sources emitting in the 300-475 nm wavelength range, especially those emitting at 365 nm, 390 nm, or 395 nm, examples of suitable free-radical photoinitiators absorbing in this area include: benzoylphosphine oxides, such as, for example, 2,4,6-trimethylbenzoyl diphenylphosphine oxide (Lucirin TPO from BASF) and 2,4,6-trimethylbenzoyl phenyl, ethoxy phosphine oxide (Lucirin TPO-L from BASF), bis(2,4,6-trimethylbenzoyl)-phenylphosphineoxide (Irgacure 819 or BAPO from Ciba), 2-methyl-1-[4-(methylthio)phenyl]-2-morpholinopropanone-1 (Irgacure 907 from Ciba), 2-benzyl-2-(dimethylamino)-1-[4-(4-morpholinyl)phenyl]-1-butanone (Irgacure 369 from Ciba), 2-dimethylamino-2-(4-methyl-benzyl)-1-(4-morpholin-4-yl-phenyl)-butan-1-one (Irgacure 379 from Ciba), 4-benzoyl-4'-methyl diphenyl sulphide (Chivacure BMS from Chitec), 4,4'-bis(diethylamino) benzophenone (Chivacure EMK from Chitec), and 4,4'-bis(N,N'-dimethylamino) benzophenone (Michler's ketone). Also suitable are mixtures thereof.

Additionally, photosensitizers are useful in conjunction with photoinitiators in effecting cure with LED light sources emitting in this wavelength range. Examples of suitable photosensitizers include: anthraquinones, such as 2-methylanthraquinone, 2-ethylanthraquinone, 2-tertbutylanthraquinone, 1-chloroanthraquinone, and 2-amylanthraquinone, thioxanthones and xanthones, such as isopropyl thioxanthone, 2-chlorothioxanthone, 2,4-diethylthioxanthone, and 1-chloro-4-propoxythioxanthone, methyl benzoyl formate (Darocur MBF from Ciba), methyl-2-benzoyl benzoate (Chivacure OMB from Chitec), 4-benzoyl-4'-methyl diphenyl sulphide (Chivacure BMS from Chitec), 4,4'-bis(diethylamino) benzophenone (Chivacure EMK from Chitec).

It is possible for LED UV light sources to be designed to emit light at shorter wavelengths. For LED light sources emitting at wavelengths from between about 100 and about 300 nm, it is desirable to employ a photosensitizer with a photoinitiator. When photosensitizers, such as those previously listed are present in the formulation, other photoinitiators absorbing at shorter wavelengths can be used. Examples of such photoinitiators include: benzophenones, such as benzophenone, 4-methyl benzophenone, 2,4,6-trimethyl benzophenone, dimethoxybenzophenone, and 1-hydroxyphenyl ketones, such as 1-hydroxycyclohexyl phenyl ketone, phenyl (1-hydroxyisopropyl)ketone, 2-hydroxy-1-[4-(2-hroxyethoxy)phenyl]-2-methyl-1-propanone, and 4-isopropylphenyl(1-hydroxyisopropyl)ketone, benzil dimethyl ketal, and oligo-[2-hydroxy-2-methyl-1-[4-(1-methylvinyl)phenyl]propanone] (Esacure KIP 150 from Lamberti).

LED light sources can also be designed to emit visible light. For LED light sources emitting light at wavelengths from about 475 nm to about 900 nm, examples of suitable free radical photoinitiators include: camphorquinone, 4,4'-bis(diethylamino) benzophenone (Chivacure EMK from Chitec), 4,4'-bis(N,N'-dimethylamino) benzophenone (Michler's ketone), bis(2,4,6-trimethylbenzoyl)-phenylphosphineoxide ("BAPO," or Irgacure 819 from Ciba), metallocenes such as bis (eta 5-2-4-cyclopentadien-1-yl) bis[2,6-difluoro-3-(1H-pyrrol-1-yl)phenyl]titanium (Irgacure 784 from Ciba), and the visible light photoinitiators from Spectra Group Limited, Inc. such as H-Nu 470, H-Nu-535, H-Nu-635, H-Nu-Blue-640, and H-Nu-Blue-660.

In one embodiment of the instant claimed invention, the light emitted by the LED is UVA radiation, which is radiation with a wavelength between about 320 and about 400 nm. In one embodiment of the instant claimed invention, the light emitted by the LED is UVB radiation, which is radiation with a wavelength between about 280 and about 320 nm. In one embodiment of the instant claimed invention, the light emitted by the LED is UVC radiation, which is radiation with a wavelength between about 100 and about 280 nm.

The liquid radiation curable resin for additive manufacturing can include any suitable amount of the free-radical photoinitiator, for example, in certain embodiments, in an amount up to about 10 wt % of the resin composition, in certain embodiments, from about 0.1 to about 10 wt % of the resin composition, and in further embodiments from about 1 to about 6 wt % of the resin composition.

Stabilizers

Stabilizers are often added to the resin compositions in order to prevent a viscosity build-up, for instance a viscosity build-up during usage in a solid imaging process. Useful stabilizers include those described in U.S. Pat. No. 5,665,792, the entire disclosure of which is hereby incorporated by reference. The inventor has surprisingly found that the presence of additional stabilizers is not needed to prevent a long-term viscosity build-up when the specific reagents are used in the stated concentrations and ratios listed in accordance with embodiments of the invention. In a preferred embodiment, therefore, the resin composition comprises less than 3% of a stabilizer, more preferably, less than 2% of a stabilizer, even more preferably less than 1% of a stabilizer, even more preferably less than 0.5% of a stabilizer, even more preferably less than 0.1% of a stabilizer, even more preferably less than 0.5% of a stabilizer, and most preferably less than 0.03% of a stabilizer (herein considered to be "substantially free" of a stabilizer).

In other aspects of the invention, the resin composition may nonetheless contain a stabilizer. If present, such stabilizers are usually hydrocarbon carboxylic acid salts of group IA and IIA metals. Most preferred examples of these salts are sodium bicarbonate, potassium bicarbonate, and rubidium carbonate. Solid stabilizers are generally not preferred in filled resin compositions. If present, a 15~23% sodium carbonate solution is preferred for formulations of this invention with recommended amounts varying between 0.05 to 3.0% by weight of resin composition, more preferably from 0.05 to 1.0 wt %, more preferably from 0.1 to 0.5% by weight of resin composition. Alternative stabilizers include polyvinylpyrrolidones and polyacrylonitriles.

Other Components

Other possible additives include dyes, pigments, talc, glass powder, alumina, alumina hydrate, magnesium oxide, magnesium hydroxide, barium sulfate, calcium sulfate, calcium carbonate, magnesium carbonate, silicate mineral, diatomaceous earth, silica sand, silica powder, titanium oxide, aluminum powder, bronze powder, zinc powder, copper powder, lead powder, gold powder, silver dust, glass fiber, titanic acid potassium whisker, carbon whisker, sapphire whisker, beryllia whisker, boron carbide whisker, silicon carbide whisker, silicon nitride whisker, glass beads, hollow glass beads, metaloxides and potassium titanate whisker), antioxidants, wetting agents, photosensitizers for the free-radical photoinitiator, chain transfer agents, leveling agents, defoamers, surfactants and the like.

Other possible additives include an inorganic filler. The inorganic filler preferably comprises silica ($SiO_2$) nanoparticles or microparticles, or nanoparticles or microparticles that are substantially silica based, for instance, greater than 80 wt %, more preferably 90 wt %, more preferably 95 wt % of silica. Preferred silica nanoparticles are Nanopox products from Nanoresins, such as Nanopox A610. Suitable examples of such silica microparticles are NP-30 and NP-100 from AGC Chemicals, SUNSPACER™ 04.X and 0.4× ST-3 from Suncolor Corporation. Examples of such silica nanoparticles are SUNSPHERES™ 200 nm such as 0.2 and 0.2-STP-10. Please see U.S. Pat. No. 6,013,714 for further examples of silica particles. However, depending on the size and other properties of the silica nanoparticles or microparticles, the thermal-stability of the liquid radiation curable resin may decrease when certain silica nanoparticles or microparticles are added to the liquid radiation curable resin due to the acidity of the silica.

The liquid radiation curable resin composition for additive manufacturing of the invention can further include one or more additives selected from the group consisting of bubble breakers, antioxidants, surfactants, acid scavengers, pigments, dyes, thicknneners, flame retardants, silane coupling agents, ultraviolet absorbers, resin particles, core-shell particle impact modifiers, soluble polymers and block polymers, organic fillers, inorganic fillers, or organic-inorganic hybrid fillers of sizes ranging from about 8 nanometers to about 50 microns. If present, the invention preferably comprises a limited amount of such fillers, as they increase the viscosity of the associated liquid radiation curable resin composition.

The second aspect of the claimed invention is a process for forming a dental aligner mold comprising:

(1) placing a first liquid layer of a liquid radiation curable resin composition, thereby forming a surface, wherein the liquid radiation curable resin composition is as defined in claim 3;

(2) exposing the first liquid layer imagewise to actinic radiation to form an imaged cross-section, wherein the radiation is of sufficient intensity to cause substantial curing of the first liquid layer in the exposed areas, thereby forming a first cured layer;

(3) lowering the first cured layer in a direction substantially orthogonal to, and away from, the surface, thereby allowing a new layer of liquid radiation curable resin composition to freely flow over the first cured layer without a recoating operation;

(4) exposing said new layer from step (3) imagewise to actinic radiation to form an additional imaged cross-section, wherein the radiation is of sufficient intensity to cause substantial curing of the new layer in the exposed areas and to cause adhesion to the first cured layer; and (5) repeating steps (3) and (4) a sufficient number of times in order to build up a dental aligner mold.

In the above, "exposing" refers to irradiating with actinic radiation.

The process of the second aspect of the claimed invention may additionally comprise a step of: (6) vacuum-forming a thermoplastic sheet over the three-dimensional dental aligner mold to form a dental aligner.

The process of the second aspect of the invention may be performed by utilizing a liquid radiation curable resin composition for additive manufacturing as described herein. It is preferred that the resin has a viscosity, when measured at 30 degrees Celsius of below 300 cps, more preferably 250 cps, even more preferably 200 cps, and most preferably 150 cps. In a further preferred embodiment, the resin may have a viscosity of as low as 75 cps at 30 degrees Celsius. The radiation used to cure the liquid layer cross sections may be by laser or LED light, at wavelengths and by light sources described previously herein. Furthermore, the low-viscosity resin used in the process of the second aspect of the invention allows for a new layer application by means of deep-dipping. That is, after cure of a layer, a new liquid layer is applied by lowering the build surface in a direction substantially orthogonal to, and away from, the source of the actinic radiation to immerse the build part in a vat of uncured, liquid resin. Shortly after immersion, the liquid resin freely flows over the previously cured layer at a specified depth determined by the orthogonal downward distance of the build surface. A resin according to the present invention therefore quickly equilibrates, such that actinic radiation may be applied to a fresh layer soon after the deep-dipping process, and without need for a recoating blade to mechanically smooth the liquid. Furthermore, a resin according to the present invention obviates the need for a pre-programmed "dwell time," or a delay factored in during a part build to account for additional resin equilibration after the recoating step, but before exposure to actinic radiation.

The third aspect of the claimed invention is the dental aligner mold created by the process according to the second aspect of the claimed invention.

The following examples further illustrate the invention but, of course, should not be construed as in any way limiting its scope.

EXAMPLES

These examples illustrate embodiments of the liquid radiation curable resins for additive manufacturing of the instant invention. Table 1 describes the various components of the liquid radiation curable resins for additive manufacturing used in the present examples.

TABLE 1

| Component | Function in Formula | Chemical Descriptor | Supplier |
|---|---|---|---|
| Chivacure 1176 | Cationic Photoinitiator | A mixture of: bis[4-diphenylsulfoniumphenyl]sulfide bishexafluoroantimonate; thiophenoxyphenylsulfonium hexafluoroantimonate and propylene carbonate. | Chitec |
| EPON 825 | Cationic Polymerizable compound | Bisphenol A diglycidyl ether | Momentive |
| Irgacure 184 | Radical Photoinitiator | 1-Hydroxy-1-cyclohexyl phenyl ketone | BASF |
| Irganox 1035 | Stabilizer | Thiodiethylene bis(3,5-di-tert-butyl-4-hydroxyhydrocinnamate) | BASF |
| Longnox 10 | Stabilizer | Neopentanetetrayl 3,5-di-tert-butyl-4-hydroxyhydrocinnamate | BASF |
| OXT-101 | Cationic Polymerizable Compound | 3-Ethyl-3-oxetanemethanol | Toagosei |
| PVP | Stabilizer | Polyvinylpyrrolidone | Various |
| SR-399LV, J | Radical Polymerizable Compound | Dipentaerythritol monohydroxypentaacrylate | Sartomer |
| TERATHANE 1000 | Chain transfer agent for cationic monomers | Poly(tetramethylene ether) glycol | Invista |
| Celloxide 2021P | Cationic Polymerizable Compound | 3,4-Epoxycyclohexylmethyl 3',4'-epoxycyclohexanecarboxylate | Dicel |
| Water | Solvent | Dihydrogen monoxide | Various |

Examples 1-6 and Comparative Examples 1-5

Various liquid radiation curable resins for additive manufacturing were prepared according to well-known methods in the art, employing varying amounts of a cycloaliphatic epoxy, a diglycidyl ether, a monofunctional oxetane, a radically polymerizable component, and a photoinitiating package. Similar resin compositions were then prepared with reduced quantities of the cycloaliphatic epoxy component. These samples were tested according to the methods for viscosity, Young's modulus, Tg, and Tg after heat treatment, dimensional stability, hydrolytic stability, and viscosity stability, as detailed below. The results are presented in Table 2.

Viscosity

The viscosity of each sample was taken with an Anton Paar Rheoplus Rheometer (S/N 80325376) using a Z3/Q1 measuring cylinder (S/N 10571) with a 25 mm diameter. The temperature was set at 30° Celsius with a shear rate of 50 s$^{-1}$. The rotational speed was set at 38.5 min$^{-1}$. The measuring container was a H-Z3/SM cup (diameter 27.110 mm) which was filled with 14.7 grams of sample (enough to the spindle). Measurements were recorded in millipascal-seconds (mPa·s), but converted and reported herein as centipoise (cps).

Measurement of Young's Modulus & Elongation at Break

Samples were tested in accordance with ASTM D638-10, except as modified as described herein. Samples were built by a Viper SLA machine (S/N 03FB0244 or S/N 02FB0160), manufactured by 3D Systems, Inc., to the standard, art-recognized Type I "dogbone" shape with an overall length of 6.5 inches, an overall width of ¾ of an inch (0.75 inches), and an overall thickness of ⅛ of an inch (0.125 inches). Samples were conditioned for 7 days at 23° Celsius at 50% relative humidity. The conditioning period exceeds the minimum prescribed in the ASTM 618-13 standard to ensure maximum stabilization in the cationic cure of the hybrid system. The samples were measured and then placed in the Sintech tensile-tested S/N using the 6500 N load cell S/N # with a 50% extensometer SN#. The speed of testing was set at 5.1 mm/min with a nominal strain rate of 0.1 mm/min at the start of test. The Young's modulus or Modulus of Elasticity was calculated by extending the initial linear portion of the load-extension curve and dividing the difference in stress corresponding to any segment of the section on this straight line by the corresponding difference in strain. All elastic modulus values were computed using the average original cross sectional area in the gage length segment of the specimen in the calculations. The Percent Elongation at break was calculated by reading the extension at point of specimen rapture and dividing that extension by the original gage length and multiplying by 100. Standard deviations were calculated according to known statistical methods.

Measurement of Glass Transition Temperature (Tg) and Glass Transition Temperature after Thermal Cure (Tg, Cure)

Glass Transition Temperature (Tg) was determined by Dynamic Mechanical Analysis according to ASTM E1640-04, unless noted as an exception herein. Samples were created by the Viper SLA machine (S/N 03FB0244 or S/N 02FB0160), manufactured by 3D Systems, Inc., using a single layer exposure with dimensions of 2.5 inches in length, 0.5 inches in width and 0.015 inches in thickness. Samples were then placed in a post-curing apparatus (PCA) for 30 minutes (15 minute per side). Samples were then placed on a Dynamic Mechanical Analysis (DMA); model RSA G2, serial number 4020-0041. The samples were mechanically oscillated with a strain amplitude of 0.05%. The tests were conducted from 0° Celsius to 160° Celsius with a heating rate of 2.0° C./min and an angular frequency of 6.2832 rad/s. There exists two rapid decreases in the storage modulus (and two rapid increases in loss modulus) along the curves generated by the Dynamic Mechanical Analysis. The first represents the glass transition temperature (calculated by the peak of the tan delta curve) of a sample after stereolithography cure. The heat for the DMA ramp changes the properties of the materials giving rise to a second rapid decrease in the storage modulus (and a second rapid increase in loss modulus). This represents the glass transition temperature of the material after further post thermal treatment, such as a 6 hour thermal bake at 100° or 140° Celsius. The second glass transition is calculated by the second tan delta peak.

Mold Dimensional Stability—At Various Steps in a Dental Aligner Manufacturing Process In one test of dimensional stability, samples were created by the viper SLA machine (S/N 03FB0244 or S/N 02FB0160), manufactured by 3D Systems, Inc. to the standard, art-recognized Type I "dogbone" shape with an overall length of 6.5 inches, an overall width of ¾ of an inch (0.75 inches), and an overall thickness of ⅛ of an inch (0.125 inches) as described in ASTM D638-10. The samples were conditioned at least 40 hours at 23° Celsius and 50% RH as described in ASTM method D618-13. The samples overall length, width of narrow section, and thickness were measure using calipers to the nearest 0.01 mm. The sample were then post treated as recorded in each individual result and measured again after treatment. This measure of dimensional stability, called $\Delta D_{FORMATION}$, is representative of parts having been cured by a stereolithography process, but prior to thermal treatment.

To simulate the dimensional stability of a sample after the vacuum forming process wherein an aligner mold is fashioned against a mold, samples were created by the Viper SLA machine to be 3 inches (length) by 1 inch (width) ⅛ inch (thickness). The samples were conditioned at least 40 hours at 23° C. and 50% RH as described in ASTM method D618-13. The samples' length, width, and thickness were measure using calipers to the nearest 0.01 mm. The samples were then placed in a vacuum former. A thermoplastic sheet of 0.8 mm thick polyethylene terephthalate (PETG) was heated to above its softening temperature of 121° C. (~150° C. was ideal). The PETG sheet was lowered onto the sample and vacuum formed for 10 seconds. The sample was then removed from the PETG sheet and its dimensions measured immediately after removal. The samples was allowed to cool for 2 hours and then measured again. This measure is represented by the notation $\Delta D_{VACUUM}$.

Hydrolytic Stability

A measure of a cured part's ability to withstand high-humidity environments over a prolonged period is simulated by a watersoak test, in accordance with ASTM D570-98. Samples were created by a Viper SLA machine (S/N 03FB0244 or S/N 02FB0160) to the dimensions of 3 inches (length) by 1 inch (width) by ⅛ inch (thickness). The samples were conditioned in an oven for 24 hours at 50° C., then cooled in a desiccator and weighed to the nearest 0.001 gram. The samples were then submersed in distilled water and maintained at 23° C. for 24 hours. Samples were removed from the water and wiped off with a dry cloth and immediately weighed again to the nearest 0.001 gram. The percent water increase was calculated by the following equation.

$$\text{Increase in weight, \%} = \frac{\text{wet weight} - \text{conditioned weight}}{\text{conditioned weight}} \times 100$$

Viscosity Stability

Forty grams of each sample was measured and placed in a 50° C.±2° C. oven. At the appropriate interval each sample was removed from the oven, then placed in a centrifuge at 2500 rpm for 1 minute (to remix any separation that might have occurred). Upon removal from the centrifuge, viscosity measurements were taken according the viscosity method listed above. Samples were then placed back into the oven to resume the test. Measurements were recorded in millipascal-seconds (mPa·s), but converted and reported herein as centipoise (cps).

TABLE 2

| Values are listed in parts by weight | | | | | | |
|---|---|---|---|---|---|---|
| Component\Formula | Example 1 | Example 2 | Example 3 | Example 4 | Example 5 | Example 6 |
| CHIVACURE 1176 | 1.65 | 1.65 | 1.65 | 1.65 | 1.65 | 1.65 |
| EPON 825 | 21 | 21 | 11 | 11 | 21 | 11 |
| IRGACURE 184 | 1.4 | 1.4 | 1.4 | 1.4 | 1.4 | 1.4 |
| OXT-101 | 7.75 | 10.95 | 24.2 | 7.75 | 9.75 | 13.25 |
| SR 399 | 5.5 | 5.5 | 5.5 | 5.5 | 7.95 | 11 |
| TERATHANE 1000 | | | | | | |
| CELLOXIDE 2021P | 12.7 | 9.5 | 6.25 | 22.7 | 8.25 | 11.7 |
| Initial Viscosity | 276.2 | 202.7 | 59.05 | 164.4 | 252.2 | 145 |
| Young's Modulus | 2436 | 2444 | 1249.832 | 2554 | 2574 | 1966 |
| Standard deviation | 182 | 199 | 800 | 310 | 219 | 260 |
| Elongation at break | 0.025 | 0.037 | 0.033 | 0.032 | 0.026 | 0.027 |
| Standard deviation | 0.012 | 0.008 | 0.013 | 0.007 | 0.002 | 0.017 |
| Tg, ° C. | 55 | 58 | 49 | 55 | 43 | 45 |
| Tg, cure, ° C. | 107 | 90 | 55 | 110 | 110 | 90 |
| $\Delta D_{VACUUM}$ | No data | No data | No data | 0.31 | No data | No data |
| Standard deviation | No data | No data | No data | ±.05% | No data | No data |
| Hydrolytic Stability | No data | No data | No data | 0.378 | No data | No data |
| Standard deviation | No data | No data | No data | ±.005% | No data | No data |
| Viscosity; Day 1 | No data | No data | No data | 179 | No data | No data |
| Viscosity; Day 6 | No data | No data | No data | 160.1 | No data | No data |
| Viscosity; Day 11 | No data | No data | No data | 164.5 | No data | No data |
| Suitability for dental molds? | Potentially suitable | Potentially suitable | Potentially suitable | Potentially suitable | Potentially suitable | Potentially suitable |

| Component\Formula | Comp. Ex. 1 | Comp. Ex. 2 | Comp. Ex. 3 | Comp. Ex. 4 | Comp. Ex.5 |
|---|---|---|---|---|---|
| CHIVACURE 1176 | 1.65 | 1.65 | 1.65 | 1.90 | 2.01 |
| EPON 825 | 21 | 21 | 21 | 24.01 | |
| IRGACURE 184 | 1.4 | 1.4 | 1.4 | 1.61 | 2.90 |
| OXT-101 | 14.2 | 7.7 | 11 | 8.93 | 5.31 |
| SR 399 | 5.5 | 12 | 8.75 | 6.34 | |
| TERATHANE 1000 | | | | | 6.45 |
| CELLOXIDE 2021P | 6.25 | 6.25 | 6.25 | 7.20 | 33.33 |
| Initial Viscosity | 161.1 | 408.7 | 240.4 | 550 | 350 |
| Young's Modulus | 1980 | 2275 | 2523 | 1895 | 1901 |
| Standard deviation | 225 | 105.809 | 332 | 248 | 74.9 |
| Elongation at break | 0.030 | 0.021 | 0.027 | 0.034 | No data |
| Standard deviation | 0.008 | 0.010 | 0.006 | 0.007 | No data |
| Tg, ° C. | 55 | 55 | 55 | 55 | 58 |
| Tg, cure, ° C. | 80 | 100 | 90 | 110 | 87 |
| $\Delta D_{VACUUM}$ | No data | No data | No data | No data | 0.40 |
| Standard deviation | No data | No data | No data | No data | ±.02% |
| Hydrolytic Stability | No data | No data | No data | No data | 0.831 |
| Standard deviation | No data | No data | No data | No data | ±.033% |
| Viscosity; Day 1 | No data | No data | No data | No data | 362 |
| Viscosity; Day 6 | No data | No data | No data | No data | 447.3 |
| Viscosity; Day 11 | No data | No data | No data | No data | 1482 |
| Suitability for dental molds? | Unsuited | Unsuited | Unsuited | Unsuited | Unsuited |

Examples 7-14

Various liquid radiation curable resins for additive manufacturing were prepared according to well-known methods in the art, by employing varying amounts of known viscosity stabilizers. Only Example 7 included no stabilizer component. These samples were tested according to the methods for viscosity stability, as detailed above, after 1, 6, and 11 days. The results are presented in Table 4.

TABLE 3

| Values are listed in parts by weight | | | | | |
|---|---|---|---|---|---|
| Component | Chemical | Ex. 7 | Ex. 8 | Ex. 9 | Ex. 10 |
| Chivacure 1176 | Arylsulfonium hexafluoroantimonate cationic inititiator 50% in propylene carbonate | 264 | 264 | 264 | 264 |
| EPON 825 | Bisphenol A diglycidyl ether | 1762.1 | 1762.1 | 1762.1 | 1762.1 |
| IRGACURE 184 | a-Hydroxycyclohexyl phenyl ketone | 224 | 224 | 224 | 224 |
| OXT-101 | 3-Hydroxymethyl-3-ethyloxetane | 1252.8 | 1252.8 | 1252.8 | 1252.8 |
| SR 399 | Dipentaerythritol pentaacrylate | 880 | 880 | 880 | 880 |

TABLE 3-continued

Values are listed in parts by weight

| | | | | | |
|---|---|---|---|---|---|
| Celloxide 2021P | 3,4-Epoxycyclohexylmethyl 3',4'-epoxycyclohexanecarboxylate | 3622 | 3622 | 3622 | 3622 |
| PVP | poly vinyl pyrrolidone | | 0.0050 | 0.0050 | 0.0050 |
| longnox 10 | Neopentanetetrayl 3,5-di-tert-butyl-4-hydroxyhydrocinnamate | | | 0.996 | 0.51 |
| Irganox 1035 | Thiodiethylene bis(3,5-di-tert-butyl-4-hydroxyhydrocinnamate) | | | | |
| Water | | | | | |

| Component | Chemical | Ex. 11 | Ex. 12 | Ex. 13 | Ex. 14 |
|---|---|---|---|---|---|
| Chivacure 1176 | Arylsulfonium hexafluoro antimonate cationic inititiator 50% in propylene carbonate | 264 | 264 | 264 | 264 |
| EPON 825 | Bisphenol A diglycidyl ether | 1762.1 | 1762.1 | 1762.1 | 1762.1 |
| IRGACURE 184 | a-Hydroxycyclohexyl phenyl ketone | 224 | 224 | 224 | 224 |
| OXT-101 | 3-Hydroxymethyl-3-ethyloxetane | 1252.8 | 1252.8 | 1252.8 | 1252.8 |
| SR 399 | Dipentaerythritol pentaacrylate | 880 | 880 | 880 | 880 |
| CELLOXIDE 2021P | 3,4-Epoxycyclohexylmethyl 3',4'-epoxycyclohexanecarboxylate | 3622 | 3622 | 3622 | 3622 |
| PVP | poly vinyl pyrrolidone | 0.0050 | 0.0050 | 0.0050 | 0.0050 |
| Longnox 10 | Neopentanetetrayl 3,5-di-tert-butyl-4-hydroxyhydrocinnamate | 0.03 | | | |
| Irganox 1035 | Thiodiethylene bis(3,5-di-tert-butyl-4-hydroxyhydrocinnamate) | | 0.021 | 0.021 | 0.022 |
| Water | Dihydrogen monoxide | | | 1.009 | 0.503 |

TABLE 4

| Viscosity Stability (cps) | Comp. Ex. 5 | Ex. 7 | Ex. 8 | Ex. 9 | Ex. 10 | Ex. 11 | Ex. 12 | Ex. 13 | Ex. 14 |
|---|---|---|---|---|---|---|---|---|---|
| Day 1 | 362 | 179 | 164 | 173 | 166 | 163 | 162 | 134 | 146 |
| Day 6 | 447.3 | 160.1 | 161.6 | 179 | 168.3 | 164.6 | 160.4 | 140.2 | 149.1 |
| Day 11 | 1482 | 164.5 | 167.6 | 180.1 | 167.2 | 162.9 | 162.7 | 144 | 152.5 |

Discussion of Results

Examples 1-6 demonstrated an increased suitability for application as a dental mold because they exhibited a more desirable combination of low initial viscosity, Young's modulus, and/or a Tg after heat treatment and vacuum forming of an aligner, coupled with acceptable stability properties.

Comparative examples 1-5 comprised a large amount of diglycidyl ether relative to the cycloaliphatic epoxy component, which generally resulted in a reduced overall suitability for use in fabricating dental aligner molds. Comparative example 5 included a polyol component, and notably underperformed the polyol-free Example 4 in terms of initial viscosity, dimensional stability, hydrolytic stability, and an ability to withstand viscosity increase over time after exposure to high temperatures.

Examples 7-14 demonstrated a high level of viscosity stability, evidencing very little viscosity increase at elevated temperatures even after 11 days. The stability stands in stark contrast to the noted increase in the formulation of comparative example 5. The nature of and quantity of the stabilizer present had a negligible effect on the amount of stabilization when compared to Example 7 of the invention, which contained no stabilizer component. Thus, in an embodiment of the present invention, the presence of a stabilizer component is not necessary to promote high levels of viscosity stability desirable in liquid radiation resins for use as molds in the dental aligner manufacturing industry.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventor for carrying out the invention. Variations of those preferred embodiments may become apparent to those of ordinary skill in the art upon reading the foregoing description. The inventor expects skilled artisans to employ such variations as appropriate, and the inventor intends for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

While the invention has been described in detail and with reference to specific embodiments thereof, it will be apparent to one of ordinary skill in the art that various changes and modifications can be made therein without departing from the spirit and scope of the claimed invention.

What is claimed is:

1. A liquid radiation curable resin composition comprising, relative to the total weight of the composition:
   (a) from about 50 to about 80 wt % of an epoxy component comprising at least two different epoxy-containing compounds, said epoxy component further comprising:
      a cycloaliphatic epoxy-containing compound, and
      an epoxy compound having an aromatic glycidyl ether group;
   (b) from about 5 to about 30 wt % of an oxetane component;
   (c) a (meth)acrylate component;
   (d) a cationic photoinitiator; and
   (e) a free-radical photoinitiator;
   wherein at least 25 wt % of the epoxy component is the cycloaliphatic epoxy-containing compound;
   wherein the resin liquid radiation curable resin composition has a viscosity of between about 75 and about 300 cps at 30 degrees Celsius; and
   wherein the oxetane component consists essentially of mono-functional oxetane compounds.

2. The liquid radiation curable resin composition of claim 1, wherein at least 50 wt. % of the epoxy component is the cycloaliphatic epoxy-containing compound.

3. The liquid radiation curable resin composition of claim 1, wherein the resin composition has a viscosity of between about 75 and about 200 cps at 30 degrees Celsius, and wherein the resin composition after cure, 60 min UV post-cure, and heat treatment at 100 degrees Celsius for 6 hours, has a Glass Transition temperature (Tg) of greater than 90 degrees Celsius.

4. The liquid radiation curable resin composition of claim 1, wherein the weight ratio of the cycloaliphatic epoxy-containing compound to the epoxy compound having an aromatic glicidyl ether group is from 3:2 to 5:2.

5. The liquid radiation curable resin composition of claim 4, wherein the cycloaliphatic epoxy-containing compound is selected from the group consisting of: 3,4-epoxycyclohex-ylmethyl-3',4'-epoxycyclohexanecarboxylate, 2-(3,4-epoxy-cyclohexyl-5,5-spiro-3,4-epoxy)-cyclohexane-1,4-dioxane, bis(3,4-epoxycyclohexylmethyl)adipate, vinylcyclohexene oxide, 4-vinylepoxycyclohexane, vinylcyclohexene dioxide, bis(3,4-epoxy-6-methylcyclohexylmethyl)adipate, 3,4-ep-oxy-6-methylcyclohexyl-3',4'-epoxy-6'-methylcyclohexan-ecarboxylate, ε-caprolactone-modified 3,4-epoxycyclohex-ylmethyl-3',4'-epoxycyclohexane carboxylates, trimethylcaprolactone-modified 3,4-epoxycyclohexylm-ethyl-3',4'-epoxycyclohexane carboxylates, β-methyl-δ-valerolactone-modified 3,4-epoxycyclohexylmethyl-3',4'-epoxycyclohexane carboxylates, methylenebis(3,4-epoxycyclohexane), bicyclohexyl-3,3'-epoxide, bis(3,4-epoxycyclohexyl) with a linkage of —O—, —S—, —SO—, —SO$_2$—, —C(CH$_3$)$_2$—, —CBr$_2$—, —C(CBr$_3$)$_2$—, —C(CF$_3$)$_2$—, —C(CCl$_3$)$_2$—, or —CH(C$_6$H$_5$)—, dicyclopentadiene diepoxide, di(3,4-epoxycyclohexylmethyl) ether of ethylene glycol, ethylenebis(3,4-epoxycyclohexanecarboxylate), and epoxyhexahydrodioctylphthalate.

6. The liquid radiation curable resin composition of claim 5, wherein component (a) is present in an amount from about 60 to about 75 wt %.

7. The liquid radiation curable resin composition of claim 1, wherein the cationic photoinitiator is present in an amount from about 2 to about 10 wt %.

8. The liquid radiation curable resin composition of claim 1, wherein the free-radical photoinitiator is present in amount from about 2 to about 10 wt %.

9. The liquid radiation curable resin composition of claim 1, wherein the (meth)acrylate component is present in an amount from about 2 to about 25 wt %.

10. The liquid radiation curable resin composition of claim 1, wherein the epoxy compound having an aromatic glycidyl ether group is present in the liquid radiation curable resin composition in an amount from about 5 to about 25 wt %.

11. The liquid radiation curable resin composition of claim 1, wherein the oxetane component is defined by the following formula:

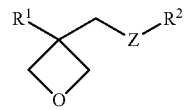

wherein R$^1$ is a C$_1$-C$_4$ alkyl group, Z is Oxygen, and R$^2$ is selected from the group consisting of H, a C$_1$-C$_8$ alkyl group or a phenylgroup.

12. The liquid radiation curable resin composition of claim 10, wherein the amount of the oxetane component (b) is from about 15 to about 20 wt %.

13. The liquid radiation curable resin composition of claim 1, wherein at least 75% of the resin composition by weight is a cationically curable component, and the epoxy compound having an aromatic glydicyl ether group is at least difunctional.

14. The liquid radiation curable resin composition of claim 13, wherein the (meth)acrylate component is a polyfunctional (meth)acrylate containing more than four functional groups.

15. The liquid radiation curable resin composition of claim 14, wherein the ratio of the cycloaliphatic epoxy-containing compound to the epoxy compound having an aromatic glycidyl ether group to the oxetane is from 1.5:1:1 to 5:2:1.

16. The liquid radiation curable resin composition of claim 15, wherein the resin composition is substantially free of a polyol.

17. The liquid radiation curable resin composition of claim 16, wherein the resin composition is substantially free of a stabilizer.

18. A process for fabricating a dental aligner mold, comprising:
  (1) placing a first liquid layer of a liquid radiation curable resin composition, thereby forming a surface, wherein the liquid radiation curable resin composition is as defined in claim 3;
  (2) exposing the first liquid layer imagewise to actinic radiation to form an imaged cross-section, wherein the radiation is of sufficient intensity to cause substantial curing of the first liquid layer in the exposed areas, thereby forming a first cured layer;
  (3) lowering the first cured layer in a direction substantially orthogonal to, and away from, the surface, thereby allowing a new layer of liquid radiation curable resin composition to freely flow over the first cured layer without a recoating operation;
  (4) exposing said new layer from step (3) imagewise to actinic radiation to form an additional imaged cross-section, wherein the radiation is of sufficient intensity to cause substantial curing of the new layer in the exposed areas and to cause adhesion to the first cured layer; and
  (5) repeating steps (3) and (4) a sufficient number of times in order to build up a dental aligner mold.

19. The process of claim 18, further comprising:
  (6) vacuum forming a thermoplastic sheet over the dental aligner mold to form a dental aligner.

20. The dental aligner mold created by the process of claim 18.

* * * * *